United States Patent
Clem

(10) Patent No.: US 6,192,736 B1
(45) Date of Patent: *Feb. 27, 2001

(54) TRIBOMETER FOR TESTING THE EFFICIENCY OF LUBRICATION UPON A RAILROAD TRACK SURFACE

(75) Inventor: George K. Clem, Chesterton, IN (US)

(73) Assignee: Diversified Metal Fabricators, Inc., Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/159,375

(22) Filed: Sep. 23, 1998

(51) Int. Cl.[7] .............................. G01N 19/02; G01B 5/00; G01B 5/28
(52) U.S. Cl. ............................ 73/9; 73/10; 73/104
(58) Field of Search ............................ 73/9, 10, 146, 73/104, 105

(56) References Cited

U.S. PATENT DOCUMENTS

| | | | |
|---|---|---|---|
| 2,496,405 | 2/1950 | Foufounis | 73/9 |
| 3,033,018 | 5/1962 | Haggadone | 73/9 |
| 3,182,513 | * 5/1965 | Mülhaupt | 73/9 X |
| 3,992,922 | 11/1976 | Noble | 73/9 |
| 4,098,111 | 7/1978 | Hardmärk et al. | 73/9 |
| 4,187,714 | * 2/1980 | Cox et al. | 73/9 |
| 4,779,447 | 10/1988 | Rath | 73/9 |
| 4,811,591 | 3/1989 | Antoine | 73/9 |
| 4,909,073 | * 3/1990 | Takahashi et al. | 73/9 X |
| 4,958,512 | 9/1990 | Johnsen | 73/9 |
| 5,331,839 | 7/1994 | Schmidt | 73/9 |
| 5,388,442 | * 2/1995 | Kumar et al. | 73/10 |

FOREIGN PATENT DOCUMENTS

| | | | |
|---|---|---|---|
| 1178889 | * 10/1964 | (DE) | 73/9 |
| 123339 | * 5/1959 | (SU) | 73/9 |
| 261751 | * 5/1970 | (SU) | 73/9 |
| 978022 | * 11/1982 | (SU) | 73/9 |

OTHER PUBLICATIONS

Abstract of SU 492412 A pub. Jan. 16, 1976 by Derwent Information LTD, ACC —No. 1977–J7761X, Derwent wreki 197640, "Rail adhesion tester–with flexible plate mounting for strain sensors and shoulders for frictio roller".*

* cited by examiner

Primary Examiner—Thomas P. Noland
(74) Attorney, Agent, or Firm—Todd Deveau; Ryan A. Schneider; Troutman Sanders LLP

(57) ABSTRACT

An automated tribometer for measuring the coefficient of friction of the tread and gauge surfaces of railroad rail is disclosed. A tribometer is provided that is pushed in front of a high-rail vehicle, wherein during operation, the tribometer extends a rail test assembly to contact the surfaces of the rail. The rail test assembly has a rail testing wheel that is urged towards contact with the rail to be tested, and eventually contacts the rail, and lastly applies a known load to the rail. The testing wheel is then dynamically braked to slow the testing wheel to the point of creepage. The automated tribometer then can calculate the coefficient of friction of the rail.

35 Claims, 12 Drawing Sheets

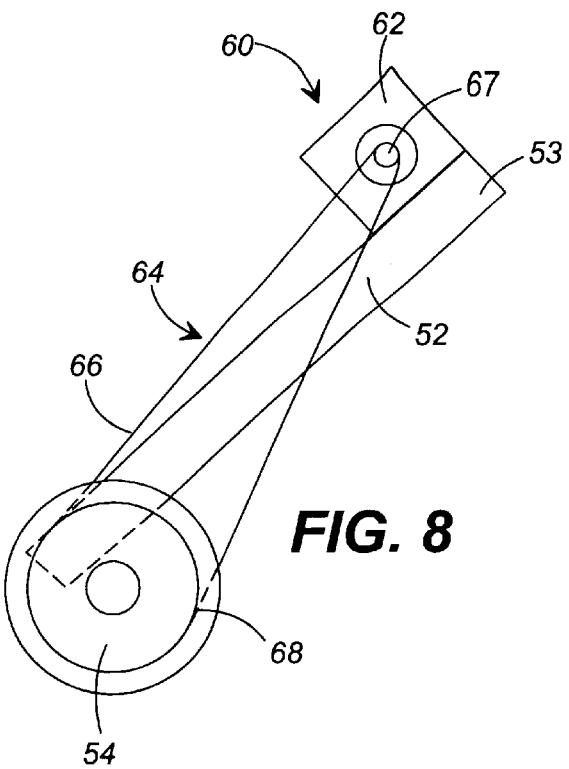
FIG. 8
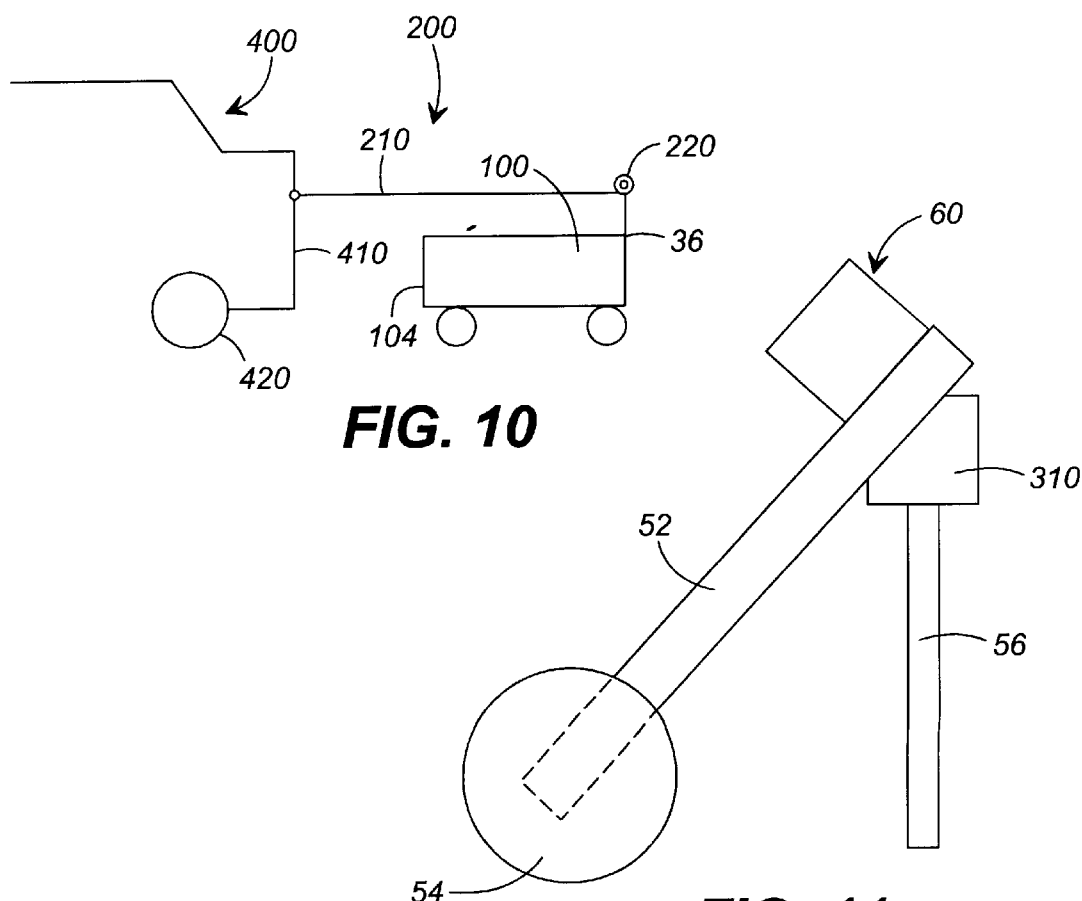
FIG. 10
FIG. 11

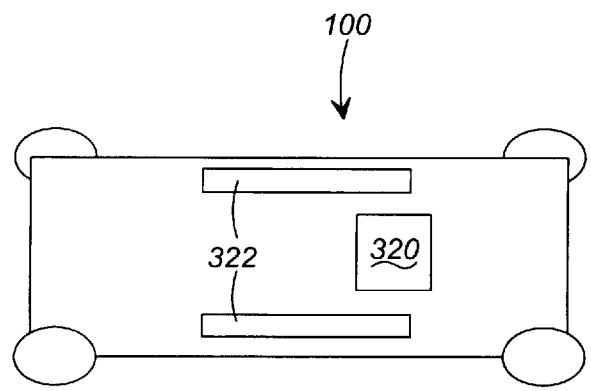
FIG. 13
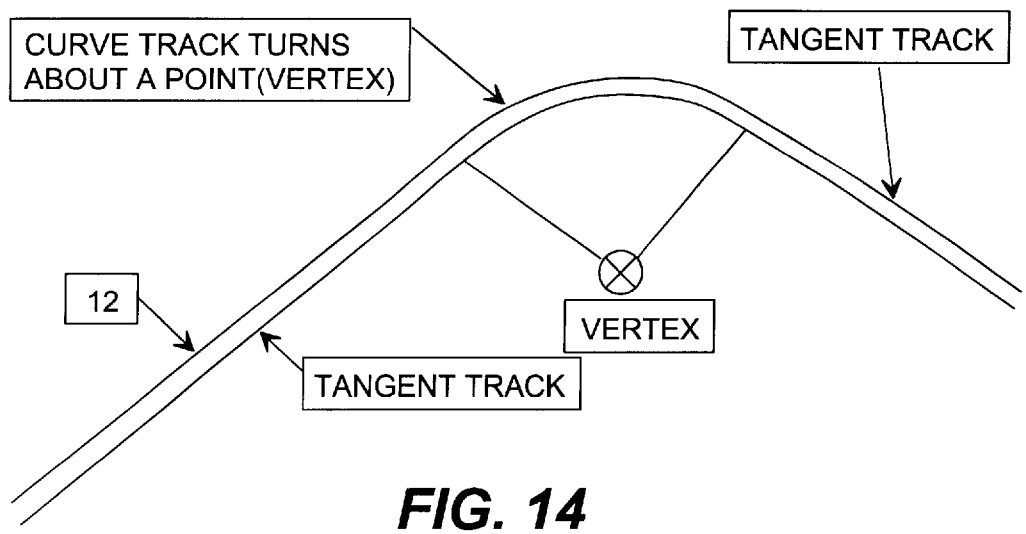
FIG. 14
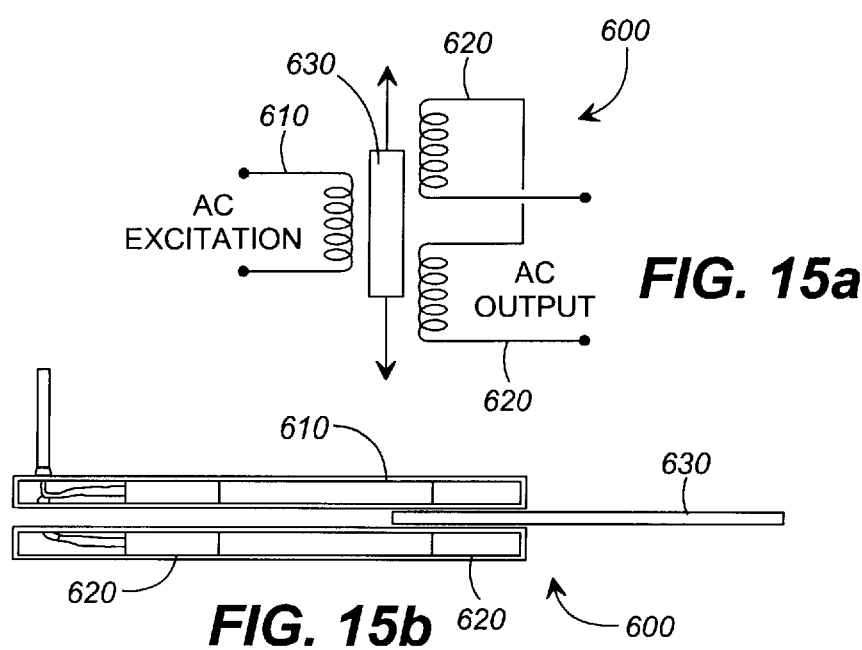
FIG. 15a
FIG. 15b

TRIBOMETER FOR TESTING THE EFFICIENCY OF LUBRICATION UPON A RAILROAD TRACK SURFACE

BACKGROUND OF THE INVENTION

1. Field of The Invention

The invention relates generally to an apparatus for measuring the coefficient of friction (COF) of a surface. In particular, the present invention relates to an apparatus for measuring the coefficient of friction of a surface of a railroad rail. The invention provides a tribometer with standard train wheels (cart wheels) that is either pushed in front of a hi-rail vehicle, or pulled by a track geometry car (or rail vehicle), which measures and records data representative of the coefficient of friction of the rail tread surface and the rail gauge surface of railroad rails. The tribometer has testing wheels, and uses "dynamic braking" to slow the testing wheels to the point of creepage, that is, just prior the point of slippage of the testing wheels upon the rails. The tribometer calculates the speed of the tribometer's testing wheels and compares it to the speed of the tribometer's cart wheels to calculate the creepage torque on the testing wheels. The creepage torque is used to determine the coefficient of friction of the rail surfaces.

2. Description of Prior Art

Railroad rails are extensively lubricated by the railroad industry to reduce both the wear of the rails and railroad car wheels, and to reduce locomotive fuel consumption. Early experiments on the benefits of lubrication utilized methods of determining lubrication effectiveness by monitoring changes in both rail/wheel forces and temperatures, as well as by visual inspection. Although useful for site-specific purposes, the measurement of forces and temperatures that changed with lubrication levels had several major drawbacks. These drawbacks included: the use of instrumentation that was usually "hard wired" to a single site and thus could not be easily relocated; the use of instrumentation that both was expensive to monitor, and required several iterations of data reduction; the comparison of raw data between different sites (before adjusting for train influences), which was difficult, if not impossible; and, the need for specific train makeup and input information such as train speed, car weight, car type, wheel profile, and recent braking history, all of which had a major effect on results, requiring careful interpretation of the data, and which made accurately determining lubrication effectiveness extremely difficult.

During the past decade, lubricating the wheel/rail interface by the railroad industry has further increased, providing improved efficiency by reducing wheel/rail resistance while extending the wear life of wheels and rails. As part of a train energy efficiency program between 1983 and 1990, the Association of American Railroads (AAR) investigated a number of methods for more accurately monitoring the effectiveness of lubrication. The AAR conducted a number of test programs at the Transportation Test Center (TTC) in Pueblo, Colo. The AAR and major railroads found that energy savings of 5–15% could be obtained with the proper application of lubricant. Since these studies were started, attempts at detailed measurements were conducted to investigate just what was the "proper application" of lubricant.

These investigative measurements were calculated, for the most part, utilizing "secondary" information, that is, information of several characteristics only tangentially related to the measurement of COF. This "secondary" information gathering required, for example, the action of a train, a moving wheel set, the monitoring of locomotive energy output, and other labor intensive and expensive actions, all to provide data that could be interpreted to determine the effectiveness of lubrication. The need for a "primary" measurement apparatus, one that took measurements directly from the rail surfaces, that was not dependent on such extensive actions, for example a passing train or obtaining information on individual train characteristics, became readily apparent early on in the AAR's energy program. The present invention is this "primary" measurement apparatus.

Over the last forty years, several devices for measuring the coefficient of friction, on both railroad rails and other surfaces, have been presented to the public. For example, U.S. Pat. No. 2,496,405 to Foufounis et al. discloses a device for measuring the degree of adhesion of vehicle wheels to a road, railway track or the like (i.e., the friction coefficient of the latter surface) wherein in one embodiment, a pair of coaxial coasters or friction wheels are made to ride upon the surface on which the vehicle moves, providing a spring which is adapted to urge the wheels toward the ground. A rotary screw and a rotary nut cooperating with the rotary screw are adapted to respond to the frictional drag of the friction wheels.

U.S. Pat. No. 3,033,018 to Haggadone discloses a wheel friction indicator comprising a displaceable metal contact block that is mounted in a gap in one rail of a track. When a railway car passes over the contact block, any frictional wheel drag, which can be caused by a defect in the axle journal bearings, will cause the contact block to rotate in the direction of movement of the car. The extent of angular displacement of the contact block is dependent on the magnitude of the frictional drag.

U.S. Pat. No. 3,992,922 to Noble discloses apparatus to predict the coefficient of friction, wherein the apparatus is placed about both rails of a railway so that both wheels of each axle of a railway vehicle can be inspected or analyzed as the vehicle is pushed towards a hump area. Braking elements extend parallel to the rails, are activated by fluid pressure, and frictionally engage opposite sides of the rotating wheels.

U.S. Pat. No. 4,098,111 to Hardmark et al. discloses a method and an apparatus for measuring road or runway properties, thus providing moving vehicles the data to compute the required retardation on a prevailing substructure. At least one measuring wheel is incorporated in a wheeled vehicle, the measuring wheel brought to engage against the substructure, at least during the measuring cycle, and to move over it with a predetermined slip, the value of which is set in relation to the speed of the wheeled vehicle.

U.S. Pat. No. 4,779,447 to Rath discloses a method for determining the coefficient of friction of a roadway. A tire on a vehicle is pressurized during normal brake operation, wherein one of the vehicle wheels is braked at a higher brake pressure than the other wheel. The method then compares the rotational speed of one wheel with the rotational speed of the other to determine the wheel slip from the difference in the rotational speeds of the wheels.

U.S. Pat. No. 4,811,591 to Antoine discloses a device for checking the surface condition of materials that will be coated with a layer of another material for protection, for either altering the material's appearance, or for subsequent assembly with other materials. The Antoine device comprises two measuring wheels. One of the wheels is progressively braked until that wheel slips along the surface of the testing material. The braking torque is measured at that time as an indication of the relative value of adhesion of the material.

U.S. Pat. No. 4,958,512 to Johnsen discloses a method and device for measuring the coefficient of friction of a surface using a wheel and a surface, particularly pneumatic tires and the surface of runways and roads.

U.S. Pat. No. 5,331,839 to Schmidt discloses a method for determining the coefficient of friction of a road surface, wherein brake pressure on a non-driven wheel or measuring wheel is increased until a tendency to lock occurs.

Many prior art tribometers used by the railroad industry are hand-operated devices. Typically, they are used in the field by railroad inspectors for spot-checking lubrication effectiveness. Since they are hand-operated devices, the speed of testing and the length of rail tested are limited to the walking speed and range of the track inspector. These devices also can weigh up to 45 pounds, making long inspection sessions difficult.

The railroad industry ran into several hurtles, overcome by the present invention, in its attempt to construct an automated tribometer. They include, among others: (1) the problem of the build up of lube, dirt, and grease in and around the device which prevents accurate measurements; (2) the problem of interference from communications equipment, for example, the operation of two-way radios and cellular phones, which can interfere with the operation of an automated tribometer, including the data collection; and (3) the disruption in operation of the apparatus upon the build up of ice, snow, and water on the tribometer, where such varying weather conditions cannot interfere with the proper operation of a dependable tribometer.

Further, preliminary investigations revealed several potential problems with moderately loaded, (100–125 lbs.) braked-wheel systems. In such designs, energy dissipation was a problem. At 35 mph, the peak power dissipation reached as high as approximately 6 HP per measurement surface. Yet, if the brake force was repeatedly ramped up until impending slip is detected, the average power dissipation is approximately 3 HP per surface. The AAR has examined some commercial brake hardware that operates in this range and, unfortunately, has found this type brake assembly too large and heavy for use with an automated tribometer. Similarly, electro-dynamic brakes appear to be inapplicable because of their weight.

Thus it can be seen that there is a need for an automated tribometer that is capable of conducting rail inspection over long, continuous segments of rail, and at higher speeds than allowed in the prior art. The tribometer must be dependable, and protected from the various adverse weather and rail conditions it will encounter. Further, the apparatus must overcome the several disadvantages of the present COF rail testing equipment. It is to the provision of such an apparatus that the present invention is primarily directed.

BRIEF SUMMARY OF THE INVENTION

Briefly described, in a preferred form, the present invention overcomes the above-mentioned disadvantages by providing a high speed apparatus that rides smoothly upon railroad track, and measures and preserves data representative of various physical properties of the track, including that of the coefficient of friction of the rails of the track. A conventional rail has two surfaces of interest in COF measurement. The running or tread surface of the rail is the generally horizontal (top) portion of the rail, while the gauge surface is the generally vertical component of the rail that is used to guide a rail vehicle along the track. As used herein, high speed is defined as any speed above the normal walking speed used in collecting the COF measurement with a hand held tribometer. The conventional hand held tribometer has a maximum operating speed of 2 mph A tribometer is used in the management of friction of railroad rails. The relationship between a steel railroad wheel and the rail is the same as any machine having components that come in contact with one another. To improve efficiency and reduce wear, the machine must be lubricated. The rail tread surface must be lubricated to reduce wheel "sticktion". This sticking and skidding causes wheel/rail noise as rail vehicles move around sharp curves. Also, rail car trucks can warp, reducing their ability to steer around curves. This effect can cause rail rollover derailments. Railroad vehicles' traction and braking are designed to operate properly when tread surfaces are lubricated to a COF of 0.35. The rail gauge face must be lubricated to reduce friction drag and wear from wheel flanges. Well-lubricated rails will reduce the possibility of wheel climb derailments. This area of the rail must have the lowest friction possible, beneficially, where COF>0.20.

Measurements of COF over 0.5 are basically measuring degrees of dryness. Railroad track that has a COF of greater than 0.5 causes the following problems:

Increased rail wear;
Increased wheel wear;
Increased use of energy (fuel);
Increased wheel-rail noise; and
Increased risk of derailment.

In use, the present invention rides along the length of track to be tested, and eases testing wheels in proximity to, and then in contact with, the running and/or gauge surface(s) of the rail. Known loads are then applied to the testing wheels while they remain in contact with the rail. The testing wheels are next subjected to dynamic braking until the point of creepage is reached for the testing wheels. The point of creepage is that point just prior to the slippage of the testing wheel. The present invention dynamically brakes the testing wheels to the point of creepage to avoid any physical deformation to the testing wheels and the rail that would occur upon wheel slippage. All the while, various measurements are collected as the tribometer moves along the track. The present tribometer can operate at speeds generally ranging from 10 to 30 mph, yet can run continuously, safely and accurately up to 35 mph for extended periods.

The present invention can be specifically used by the railroad industry to continuously measure the friction of the rails over several miles of track, thereby quantifying the true effectiveness of rail lubrication products and methods.

The tribometer is preferably designed to be pushed along the railroad track at a speed of at least 30 mph by a conventional hi-railer type vehicle used by most railroads, for example, utility trucks, pickups or Suburban-type vans, with small diameter track guide wheels mounted front and back.

The tribometer of the present invention preferably comprises a test cart, an attachment means to attach the test cart to a motive means that propels the test cart down the track, and automated systems to both control the test cart and its various assemblies, and to measure and record the various data taken during testing, including COF measurements.

The test cart of the present invention enables the tribometer to run smoothly along the train tracks, and generally supports the various control and testing systems of the present invention. Preferably, the test cart comprises a test cart frame, front and rear axle assemblies, a rail test assembly, and a braking means.

The test cart frame is the physical support mechanism, or chassis, of the present tribometer. The cart frame can be constructed of any conventional material(s) that provides sufficient strength and durability to support the various assemblies and systems of the apparatus and to enable the tribometer to travel the tracks without structural failure.

The test cart further comprises front and rear axle assemblies that support the tribometer on the tracks. Located near the front of the test cart frame is the front axle assembly having a front axle and two cart wheels. The axle is conventionally attached to the test cart frame, and is capable of free rotation about the axle's longitudinal axis. Additionally, the front axle can rotate about the longitudinal centerline of the test cart. This rotation ensures the cart wheels of the test cart are at all times in contact with the track, even if the surface of the track is warped. Located on opposite ends of the front axle are front cart wheels. Similarly, located on the rear of the test cart frame is the rear axle assembly having a rear axle and two rear cart wheels, also capable of free rotation. Preferably, the rear axle is split allowing each rear cart wheel to turn independently, which enables one or both of the rear cart wheels to be independent speed reference wheels.

The test cart frame and front and rear axle assemblies therefore provide a test cart assembly that can ride along the rails of the railroad track. The four cart wheels can be conventional railroad wheels, which keep the test cart guided firmly on the track. It will be understood by those in the art that the test cart frame and axle assemblies can comprise similar construction known in the art to provide a free-wheeling cart frame.

The test cart further comprises at least one rail test assembly. The rail test assembly is that portion of the present invention that contacts the rail surfaces, which allows the tribometer to measure and record the data necessary for COF calculations. Preferably, the rail test assembly comprises a rail test frame, at least one rail testing wheel, a rail test axle assembly, and an extension means to extend and retract the rail testing wheel to and from the surface of the tested rail. In general, the rail test assembly positions the testing wheel in communication with one of the surfaces of a rail. Then, in coordination with the braking means, (described below) the testing wheel is braked, and the various measurements taken.

The rail test frame provides similar support for the rail testing wheel as does the test cart frame for the cart wheels. Each rail testing wheel is either a tread surface testing wheel or a gauge surface testing wheel, depending on the rail surface to be tested. The rail testing wheel, unlike a cart wheel, is not a conventional railcar wheel. The tread testing wheel is flangeless and has more conicisity than a standard rail wheel. This configuration provides a consistent contact line with the tread testing surface. The gauge surface testing wheel preferably is treadless and canted which provide a consistent contact line with the gauge surface.

The rail test axle assembly generally secures the rail testing wheel to the rail test frame, while providing the rail testing wheel free rotation about a test axle. The geometry of the test assembly and of the surfaces of the test axle and rail test wheel provides for accurate and repeatable measurements at the same location on the rail. This is important as the COF varies laterally across the surface of a rail.

The extension means of the present invention both urges the rail testing wheel to the rail surface, and retracts the rail testing wheel from the rail. The rail test assembly has a testing mode and a non-testing mode, or operational/non-operational modes. When the rail test assembly is in the testing mode, the extension means of the rail test assembly eases the testing wheel into contact with the rail surface, and the various COF measurements are then taken. In the periods of non-testing, the extension means retracts the testing wheel from the rail, at which point only measurements relating to a speed reference wheel are taken, for example, speed and/or distance traveled. The cart wheels continuously are in contact with the rail, during both testing and non-testing, and thus provide the basis for odometer measurements and the like. In contrast, the rail testing wheel is in contact with the rail only during the testing mode.

The extension means not only moves the rail testing wheel between the testing/non-testing modes, but also applies a load on the testing wheel. The preferable extension means is an air cylinder. During testing, rail track anomalies cause the extension means to extend or retract as required, thus keeping the testing wheel on the rail, while exposing the entire rail test assembly to minimal danger from track anomalies. In a preferred embodiment, the extension means further comprises a pivot point around which the rail test assembly frame can pivot about the rear of the test cart frame during the rail test assembly's extension or retraction. In this embodiment, an air cylinder is attached at one end to the rear portion of the test cart frame, and at the other end to the upper end of the rail test frame (defined as the end of the rail test frame opposite the lower end of the rail test frame, the end with the rail testing wheel.)

The rail test frame is pivotally connected to the test cart frame at generally the midpoint of the rail test frame. Therefore, extension or retraction of the extension means extends or retracts the rail testing wheel to/from the rail by conversely retracting or extending the upper end of the rail test frame.

The test cart can have one of several embodiments of the number and construction of rail test assemblies. The test cart can comprise a single rail test assembly to test either the running or gauge surface of the rail. The test cart may have two separate rail test assemblies, one including a tread surface testing wheel to test the running surface of the rail, and one including a gauge surface testing wheel to test the gauge surface of the rail. The separate test assemblies may be in different modes concurrently. For example, the tribometer can test the tread surface of a rail with a tread test assembly in the testing mode, while a gauge test assembly remains in the non-testing mode and vice verse.

Further, the test cart may comprise a single rail test assembly having a single rail test frame, one rail testing wheel and a single extension means, which rail test assembly only tests the running surface of only one of the railroad rails. In another embodiment, the test cart may comprise a single rail test assembly having a single rail test assembly frame, two testing wheels and a single extension means. The two testing wheels are provided one each for the two running surfaces of the two rails. This embodiment of the present invention can then test the two running surfaces of the rail during a single pass. While utilizing a single testing wheel requires two separate passes of the tribometer over the same section of track, there can be a marked difference in the COF of each running surface of the track that cannot accurately be tested with a single rail test frame, two testing wheels and a single extension means. Supplying the same loads to the two separate testing wheels can lead to an imperfect test run.

Alternatively, the test cart can comprise two rail test assemblies, each having a rail test frame, a testing wheel and an extension means. In this embodiment, for example, if both rail test assemblies are rail tread surface test assemblies, the tread surfaces of each of the two rails of the track can be independently tested in a single pass of the tribometer.

Similarly, the test cart can comprise a gauge surface test assembly having a gauge test frame, a single gauge testing wheel and an extension means, which assembly tests the gauge surface of the railroad rail, as opposed to the running surface of the rail. The gauge surface test assembly can alternatively comprise two testing wheels to test the gauge surfaces of both rails simultaneously. Any of the above embodiments of the tread surface test assembly apply equally to a gauge surface test assembly. In yet another embodiment of the tribometer, the test cart can comprise both an embodiment of the tread surface test assembly and an embodiment of the gauge surface test assembly. For example, the cart can comprise a tread surface test assembly having two testing wheels and a gauge surface test assembly having a single test wheel.

To slow the rail testing wheel to creepage, the tribometer further comprises a braking means designed to slow the rotation of the rail testing wheel. Throughout the braking period the testing wheel remains in contact with the rail. "Dynamic braking" is used to slow the testing wheel to the point of creepage (i.e., just prior the point of slippage of the rail testing wheel). The braking means generally comprises a dynamic braking motor and transmission means to transmit the dynamic braking to the testing wheel. The rail test frame can support both the braking motor and transmission means.

Beyond the tribometer test cart, the present invention can further comprise an attachment means to attach the test cart to a motive means for propelling the tribometer down the track. The test cart can be pushed in front of the hi-rail vehicle via the attachment means. The attachment means can comprise a stiff arm pivoting from the front of the hi-rail vehicle to an attachment pivot point on the test cart. The pushing force of the hi-rail vehicle preferably extends from the vehicle as close to the ground as possible in order to prevent an up-lifting force on the rear axle. This provides for good tracking and stability.

In an alternative embodiment of the present invention, the test cart can have its own motive means to move the tribometer down the track without the use of, for example, a hi-rail vehicle or track geometry car, and, thus, the present invention would not include an attachment means. In this embodiment, the present invention can be equipped with an on-board, conventional movement means like an engine, regulator and drive train, which can provide sufficient power to the cart wheel(s) of the tribometer.

The tribometer of the present invention further comprises automated systems for the control of the several components of the tribometer and for the gathering of the various measurements taken, including COF testing, calibration, and report generation. The automated system can further provide power control to the test cart, control of the extension means of the rail test assembly and control of the dynamic braking of the testing wheel.

The automated system preferably comprises automated data collection, with direct readout (real time) of "average" friction conditions available for viewing by an operator of the push vehicle. The automated system may comprise elements that are not physically located on (on board) the present tribometer. For example, a computer or other data collection/data interpretation device may be remotely located from the tribometer, wherein the tribometer's sensors "send" the measured data to the remote computer for interpretation. In a preferred embodiment, the present invention measures the COF of both the running and gauge surfaces independently on both rails. In addition to COF measurements, the system can measure and collect data on tribometer distance from initial locations down the track or landmarks, and critical components making up the coefficient of friction calculation, such as applied forces. An odometer can be provided so that the measurements can be indexed to mileposts or other convenient reference locations.

The tribometer of the present invention incorporates several qualities and innovations over the prior art COF measurement devices for train rails. The present invention can safely traverse a variety of normal rail devices including, but not limited to, turnouts, crossovers and highway grade crossings. Further, the tribometer can also navigate safely over non-mainline rail features, such as retarders.

The present invention operates safely while meeting or exceeding the L/V ratios outlined in the AAR's desired performance specifications for a tribometer (Production Tribometer Specification, Project No. 4000, Chapter 2.4), as well as stability and other criteria, for example, the angle of attack. L/V is the ratio of lateral load (L) over vertical load (V). Lateral load is the weight applied by the rail wheel flange against the gauge face of the rail. Vertical load is the weight applied by the tread of the rail wheel to the top of the rail. L/V ratios below 0.8 are considered safe. L/V ratios above 0.8 present a possibility that the wheel flange can climb the gauge face of the rail and cause a derailment. The possibility of a derailment is reduced by a low COF on the gauge face of the rail. Additionally, the angle of the gauge face with respect to normal also can increase the risk of a derailment. Lack of lubrication causes the rail to wear, and increases this angle. Thus, measurements relating to lubrication conditions are of extreme importance. The angle of attack (AOA) for curves is defined as the angle in the horizontal plane between an axle of the tribometer and a line radial to the curve. For tangent track, AOA is defined as the angle in the horizontal plane between the axle and a line drawn perpendicular to the rails.

In relation to operating speed, the present invention is designed to operate at a minimum speed range of generally 3–35 mph, higher for use with hi-rail vehicles and even higher speeds if used with select other vehicles (i.e., track geometry vehicles).

Accordingly, it is an object of the present invention to provide an automated tribometer that is designed to meet the needs of the railroad industry as outlined by the AAR in its 1994 call for the production of a high speed tribometer.

It is a further object of the present invention to provide a tribometer having testing wheels and cart wheels, which tribometer moves on railroad rails while measuring and recording data representative of the coefficient of friction of the rail tread surface and/or the rail gauge surface.

Yet another object of the present invention is to provide a tribometer that utilizes "dynamic braking" to slow the test wheels to the point of creepage, wherein the tribometer measures the speed of the testing wheels and compares it to the speed of the cart wheels, in order to measure the creepage torque on the testing wheels.

Another object of the present invention is to provide a tribometer that overcomes the many disadvantages in the prior art designs that includes the use of instrumentation that is "hard wired" to a site and can not be easily relocated; instrumentation which is expensive to monitor and requires several iterations of data reduction; the comparison of raw data (before adjusting for train influences) between different sites, which is difficult, if not impossible; and the need for specific train makeup and input information such as speed, train car weight, car type, wheel profile, and recent braking history, all which have a major effect on results, requiring careful interpretation of the data and which makes accurately determining absolute lubrication effectiveness extremely difficult.

A further object of the invention is to provide a "primary" measuring apparatus that can successfully measure periodic COF data on train rails, that can operate successfully through the common problems of the build up of lube, dirt and grease on the apparatus, that can shield the data collection from the interference of communications equipment, for example, the operation of two-way radios and cellular phones, and can operate through the possible build up of ice, snow, or water on the tribometer.

It is yet another object of the present invention to provide a tribometer that can accurately perform COF measurements at speeds ranging from 3 to 35 mph.

Thus it can be seen that there is a need for an automated tribometer that is capable of conducting "primary" measuring and inspection of rail surfaces at higher speeds than capable in the prior art, and that is dependable and protected from various adverse weather and rail conditions. It is to the provision of such a method and apparatus that the present invention is primarily directed.

BRIEF DESCRIPTION OF THE DRAWINGS

FIG. 8 is a side view of a preferred embodiment of the braking means of the present invention.

FIG. 10 is a side view schematic of a preferred embodiment of the attachment means of the present invention.

FIG. 11 is a side view of the control system of the tread test assembly according to one embodiment of the present invention.

FIG. 13 is a top view of the power control of the test cart according to one embodiment of the present invention.

FIG. 14 is a schematic view of a curve in track.

FIGS. 15a and 15b are illustrations of a linear variable differential transformer.

DETAILED DESCRIPTION OF A PREFERRED EMBODIMENT

Figure 1:
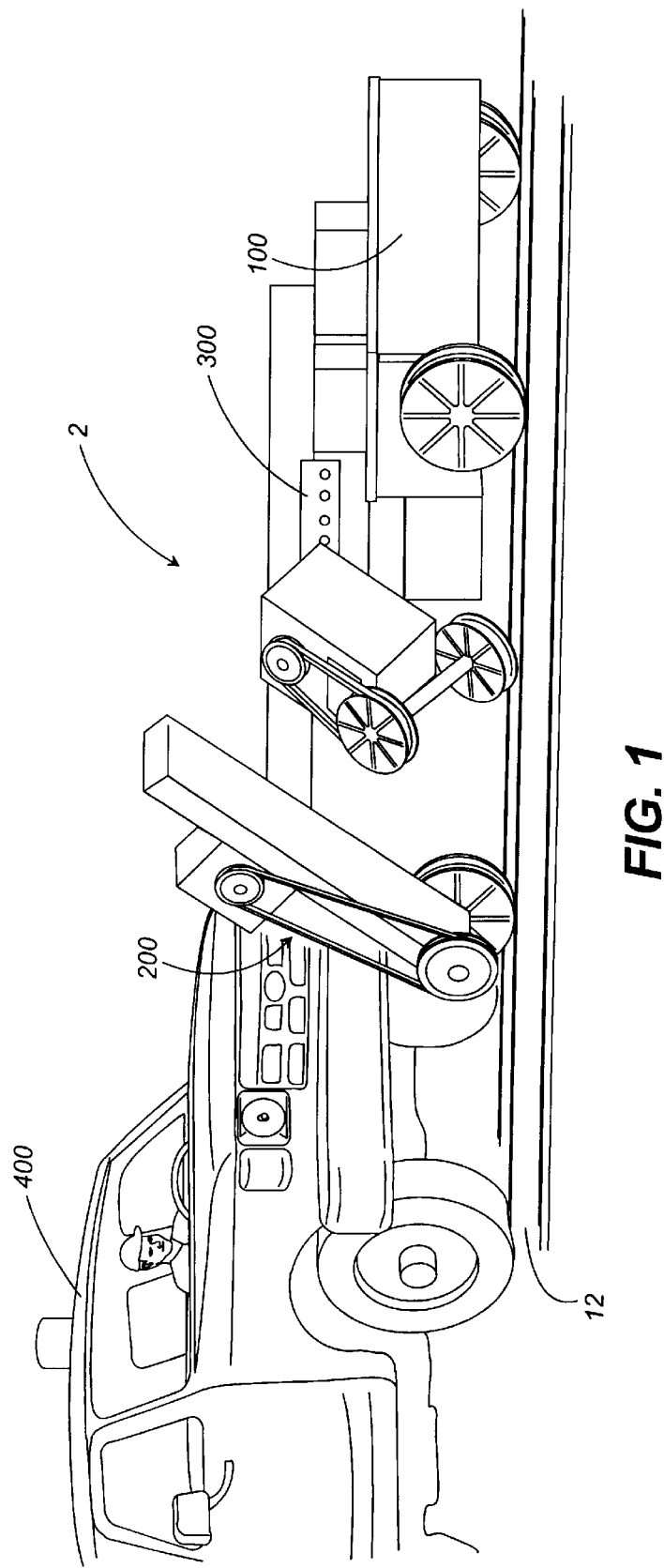
FIG. 1 is a perspective view of the tribometer of the present invention according to a preferred embodiment and attached to a hi-rail vehicle.

Referring now in detail to the drawing figures, wherein like reference numerals represent like parts throughout the several views, as shown in FIG. 1 the tribometer 2 of the present invention preferably comprises a test cart 100, an attachment means 200 to attach the test cart 100 to a motive means to propel the test cart 100 down the railroad track 12, and automated systems 300 to control the operation of the test cart 100 and measure the various data of the rails, including the COF data.

Figure 2:
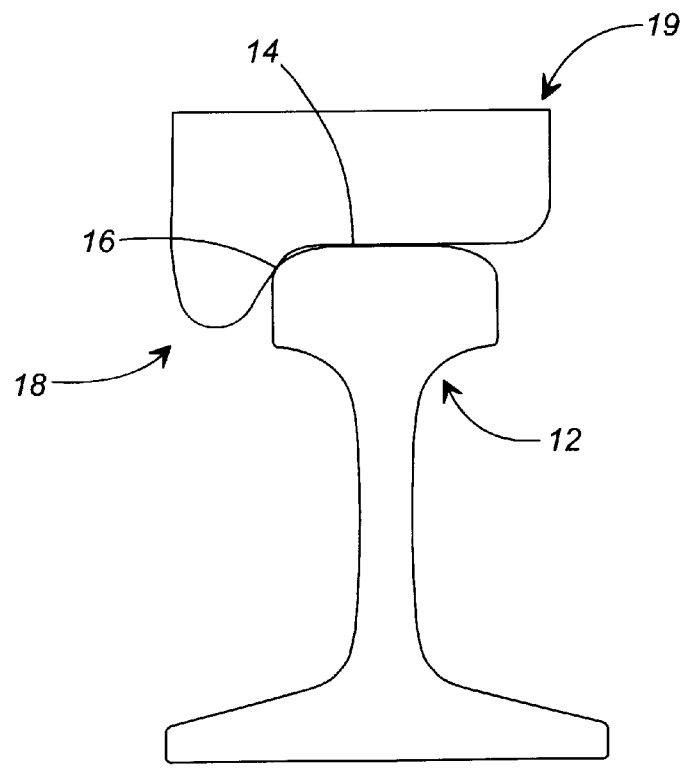
FIG. 2 is a cross sectional view of a convention railroad rail.

The tribometer 2 is designed to ride along the surface of railroad rails 12 and measure and record data relating to rail lubrication, including data representative of the coefficient of friction of preferably the rail 12 running surface 14 and the rail 12 gauge surface 16 of both rails. FIG. 2 shows a cross section of a single rail 12. The rail 12 is the right rail of a two rail track if the direction of forward travel is into the drawing figure. In this configuration, the flange portion 18 of a typical railroad wheel 19 contacts rail 12 along gauge face 16. The bulk of wheel 19 rides along the running surface 14 of rail 12.

Figure 3:
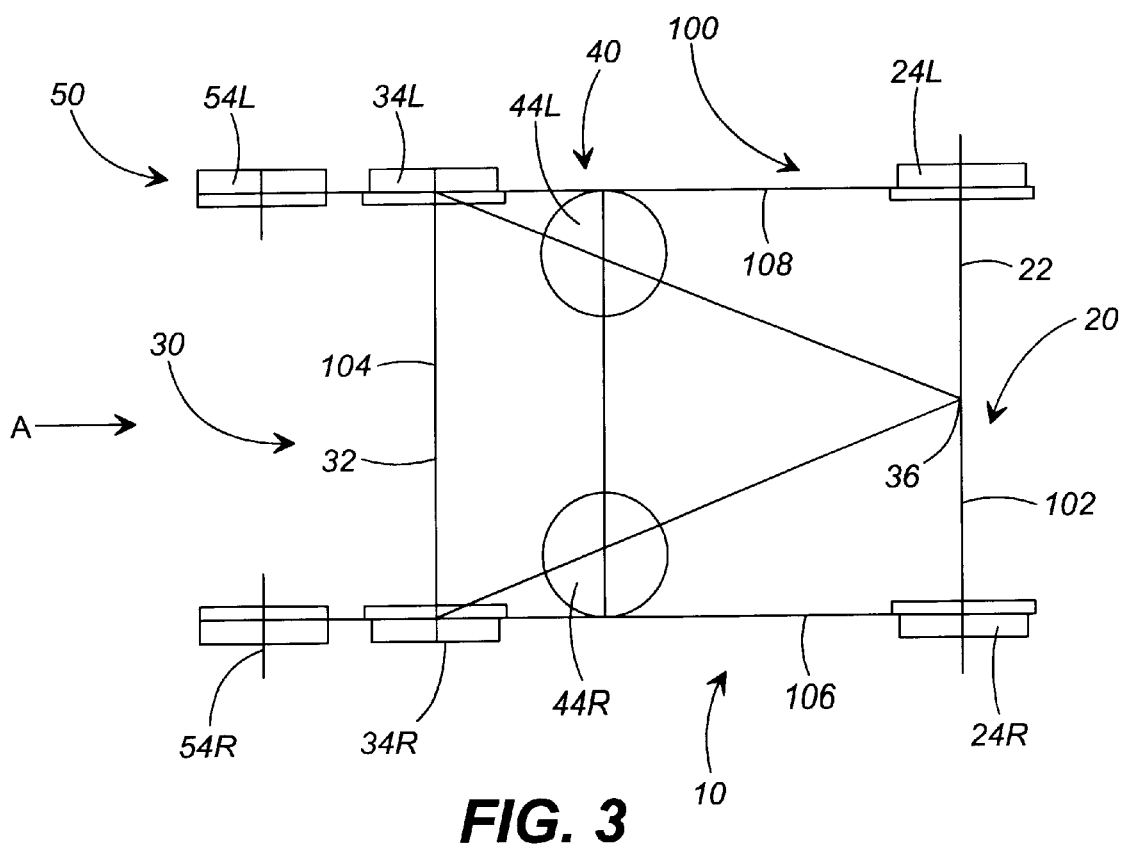
FIG. 3 is a top view schematic of a test cart according to one embodiment of the present invention.
Figure 4:
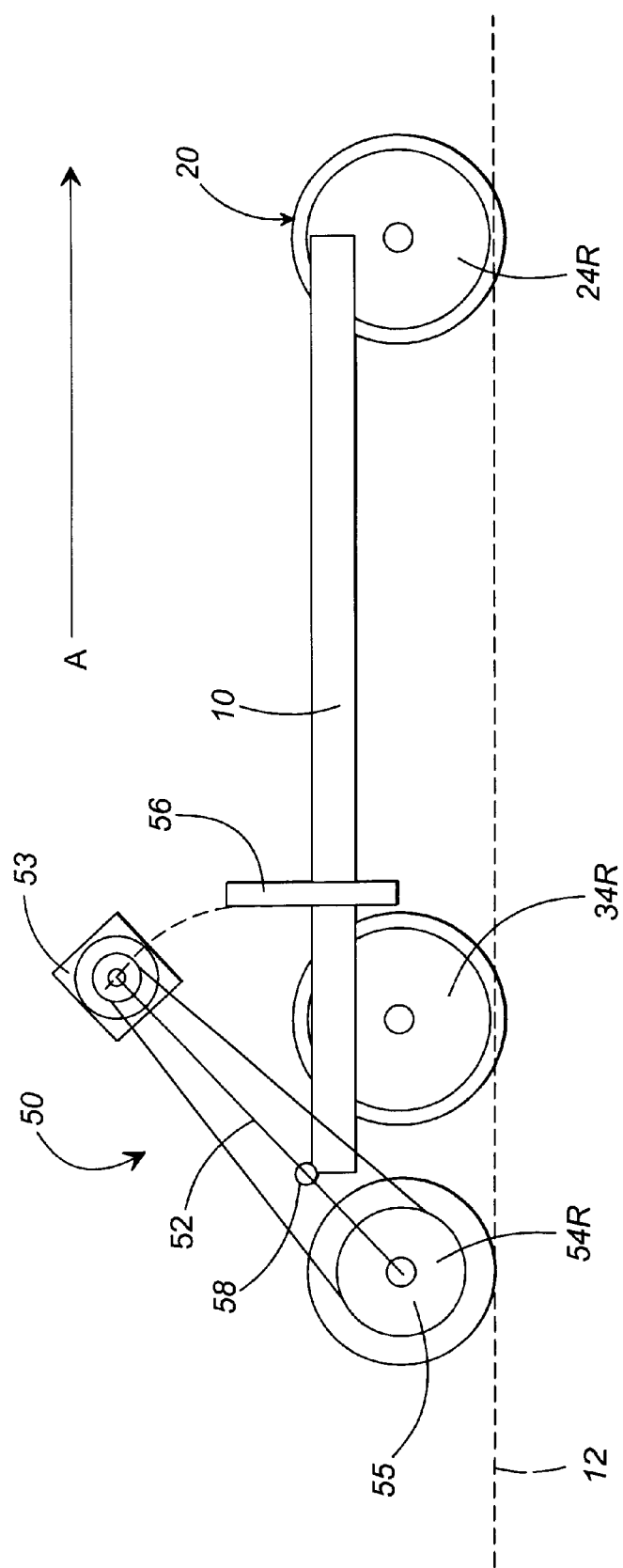
FIG. 4 is a side view schematic of a test cart according to another embodiment of the present invention.

FIGS. 3 and 4 depict schematic views of two embodiments of the test cart 100 of the present invention 2. As shown in FIG. 3, preferably the test cart 100 comprises test cart frame 10, front axle assembly 20, rear axle assembly 30, gauge surface test assembly 40, tread surface test assembly 50 and braking means 60 (not shown).

The test cart frame 10 generally comprises the chassis of the tribometer 2. Test cart frame 10 has both a front end 102 and back end 104, and right side 106 and left side 108. The preferably direction of travel of the tribometer 2 is indicated by arrow A.

The front axle assembly 20 comprises axle 22 attached in a conventional manner near the front end 102 of test cart frame 10. Axle 22 is capable of free rotation along its longitudinal axis. Located on either end of axle 22 are right front cart wheel 24R and left front cart wheel 24L (hereinafter sometimes collectively referred to simply as cart wheels 24). In a preferred embodiment, the front axle 22 can further rotate ±1.5 inches about the longitudinal centerline of the cart frame 10. This further rotation provides sufficient front axle 22 adjustment so the front cart wheels 24 are always in contact with the track even if the surface of the rails are warped. Rear axle assembly 30 comprises rear axle 32 having rear cart wheels 34R and 34L. Preferably, the rear axle 30 is split and the two sections then may rotate independent of each other. Further, rear axle assembly 20 can pivot in the vertical direction about the front axle 22 at pivot point 36 to accommodate any track 12 warpage which could derail the test cart 100 if not adequately addressed.

The test cart 100 further preferably comprises two rail test assemblies, gauge and tread test assemblies 40, 50, respectively. The gauge test assembly 40 is designed to measure and test the conditions of the gauge face 16 of rail 12. The tread test assembly 50 rides and takes measurements along the rail tread surface 14 of rail 12 during testing.

Figure 5:
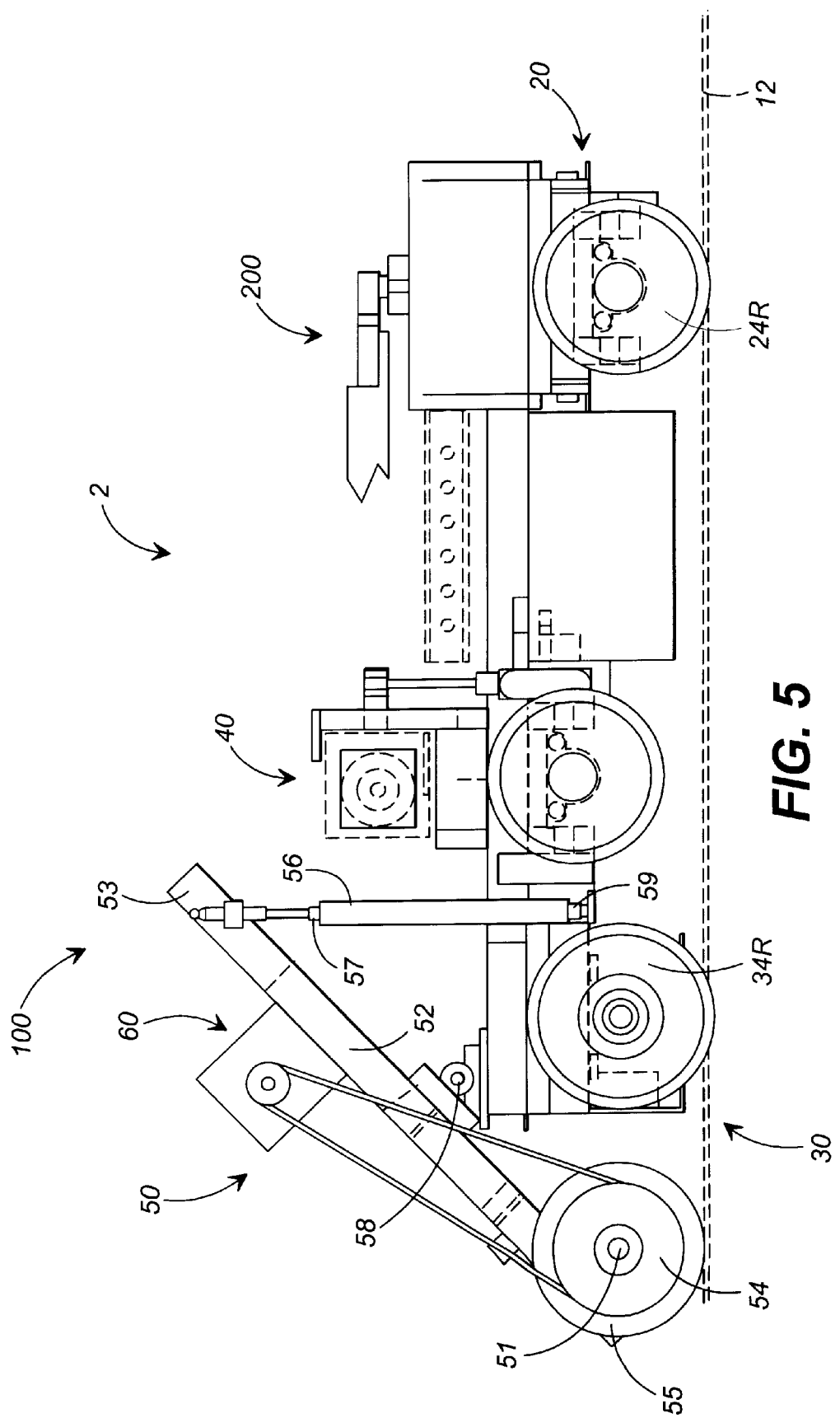
FIG. 5 is a side view of the present invention having two rail test assemblies according to a preferred embodiment.
Figure 7:
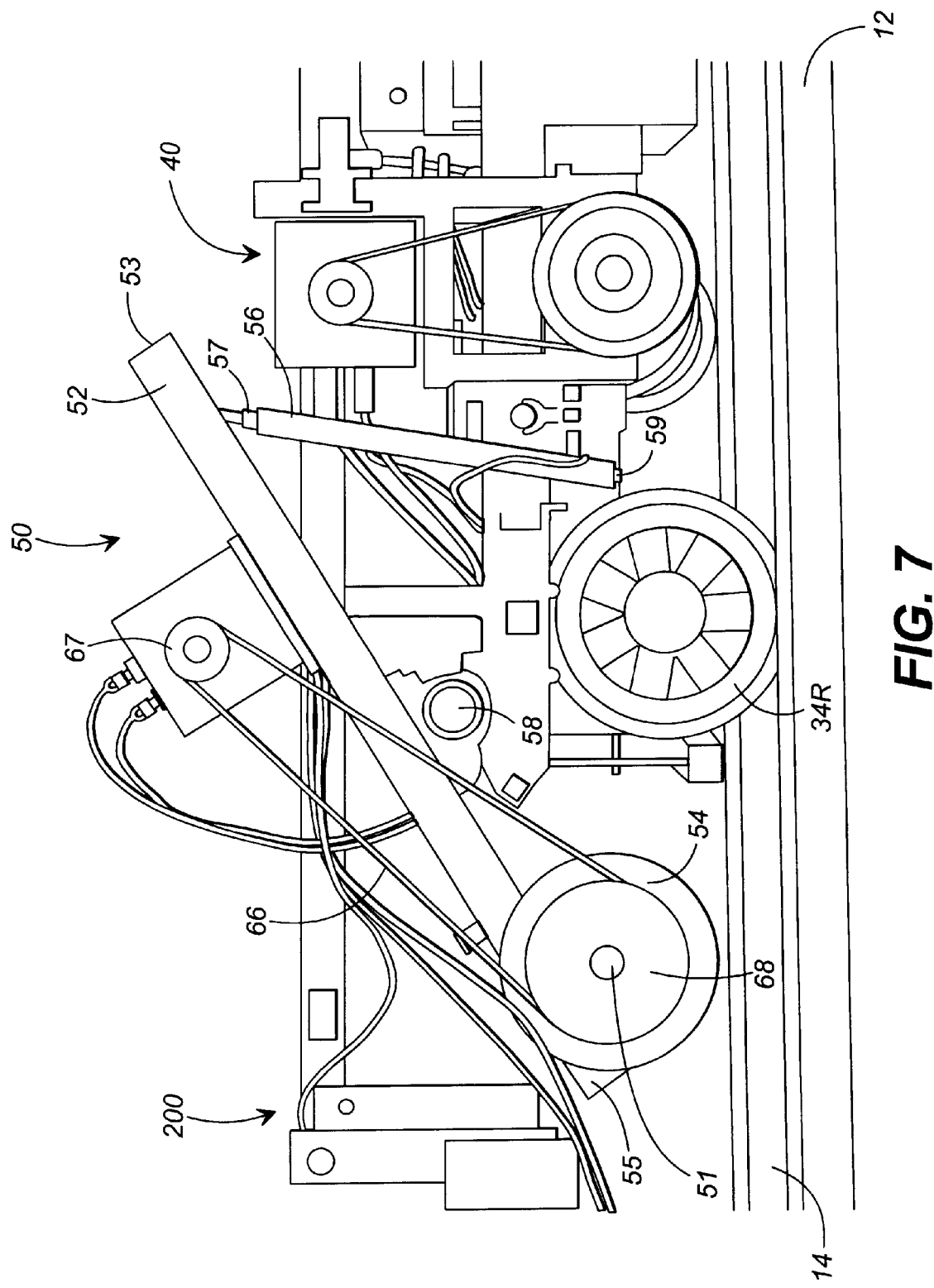
FIG. 7 is a perspective view of a tread test assembly according to a preferred embodiment of the present invention.

Shown most clearly in FIGS. 5 and 7, located near the back end 104 of the test cart 100, tread test assembly 50 comprises tread test axle 51, tread test frame 52, tread testing wheel 54 and tread extension means 56. The tread test frame 52 provides the support chassis for the tread test assembly 50 and the braking means 60. Tread test frame 52 has a lower end 55 and an upper end 53. Located at the lower end 55 of tread test frame 52, testing wheel 54 is attached to tread test frame 52 by tread test axle 51, a conventional axle/frame attachment means, for example, an axle and bearings (not shown).

Both the lower end 55 and the upper end 53 of tread test frame 52 are vertically extendible, in opposite directions, from back end 104 of test cart 100 by an extension means 56. The extension means 56 allows for both the extension and retraction of the testing wheel 54 from contact with the tread surface 14 of rail 12. In a preferred embodiment, the extension means 56 comprises air cylinder 56 and pivot 58. The opposite, vertical displacement of the lower end 55 to the back end 53 of tread test frame 52 occurs because a portion of frame 52 is pivotally connected to the back end 104 of test cart 100 at pivot 58.

A rail test assembly has two modes of operation, a testing mode, wherein the air cylinder 56 eases the testing wheel 54 of tread test assembly 50 into contact with the tread surface 14 of rail 12 and the various COF measurements are taken, and a non-testing mode, wherein the tread testing wheel 54 is retracted from the rail 12. FIG. 5 shows the tread test assembly 50 of tribometer 2 in testing mode, and FIG. 7 shows the present invention on the non-testing mode. Unlike the tread testing wheel 54, the cart wheels 24, 34 are continuously in contact with the rail 12, during both testing and non-testing. The tread testing wheel 54 is only in contact with the rail 12 during the testing operation.

When tread test assembly 50 is in the non-testing mode, tread testing wheel 54 is withdrawn from contact with rail 12, as extension means 56 enter a retracted position and, thus, the upper end 53 of tread test frame 52 is pulled down, while the lower end 55 is lifted away from rail 12. In the testing mode, as shown in FIGS. 4 and 5, the extension means 56 extends the upper end 53 of tread test frame 52, thus lowering the lower end 55 of the test frame 52, including the tread testing wheel 54, to the track 12, about the pivot point 58. As the extension means 56 continues to extend, the tread testing wheel 54 eventually contacts the running surface 14 of rail 12.

The extension means 56 can further extend tread testing wheel 54 beyond simply the initial contact with rail 12, and apply a downward load on the testing wheel 54. The total amount of force applied to the testing wheel 54 is a combination of both the unbalanced weight of the tread test assembly 50, and the additional force applied with the continued extension of extension means 56. In preferred form, as shown in FIGS. 5 and 7, extension means 56 comprises an air cylinder 56 that is attached at the rod end 57 to upper end 53 of test tread frame 52, and at the cap end 59 to the back end 104 of test cart frame 100. Rail track anomalies cause the air cylinder 56 to extend or retract the tread testing wheel 54. Air cylinder 56 provides the constant downward load on the rail 12 via the pivot 58 arrangement.

In a preferred embodiment, the air cylinder 56 is 21 inches long with the piston set 2 inches from the top of the stroke. The rod end 57 of the cylinder 56 is vented to the atmosphere. The cap end 59 of the cylinder 56 is supplied with the constant gas pressure necessary to provide the required downward load. In this arrangement, the travel of the piston is ±1 inch, although in prototype testing the actual movement was considerably less. Using Boyle's Law (wherein at a constant temperature, the volume of a given quantity of any gas varies inversely as the pressure to which the gas is subjected, expressed as PV=k), this configuration results in a load on the tread test wheel 54 maintained within ±20 lbs. (using a constant 20 psi gas pressure supply). The air pressure in the cylinder 56 typically does not vary more than ±2 psi. Further, impact loads are cushioned by the air cylinder 56.

Figure 6:
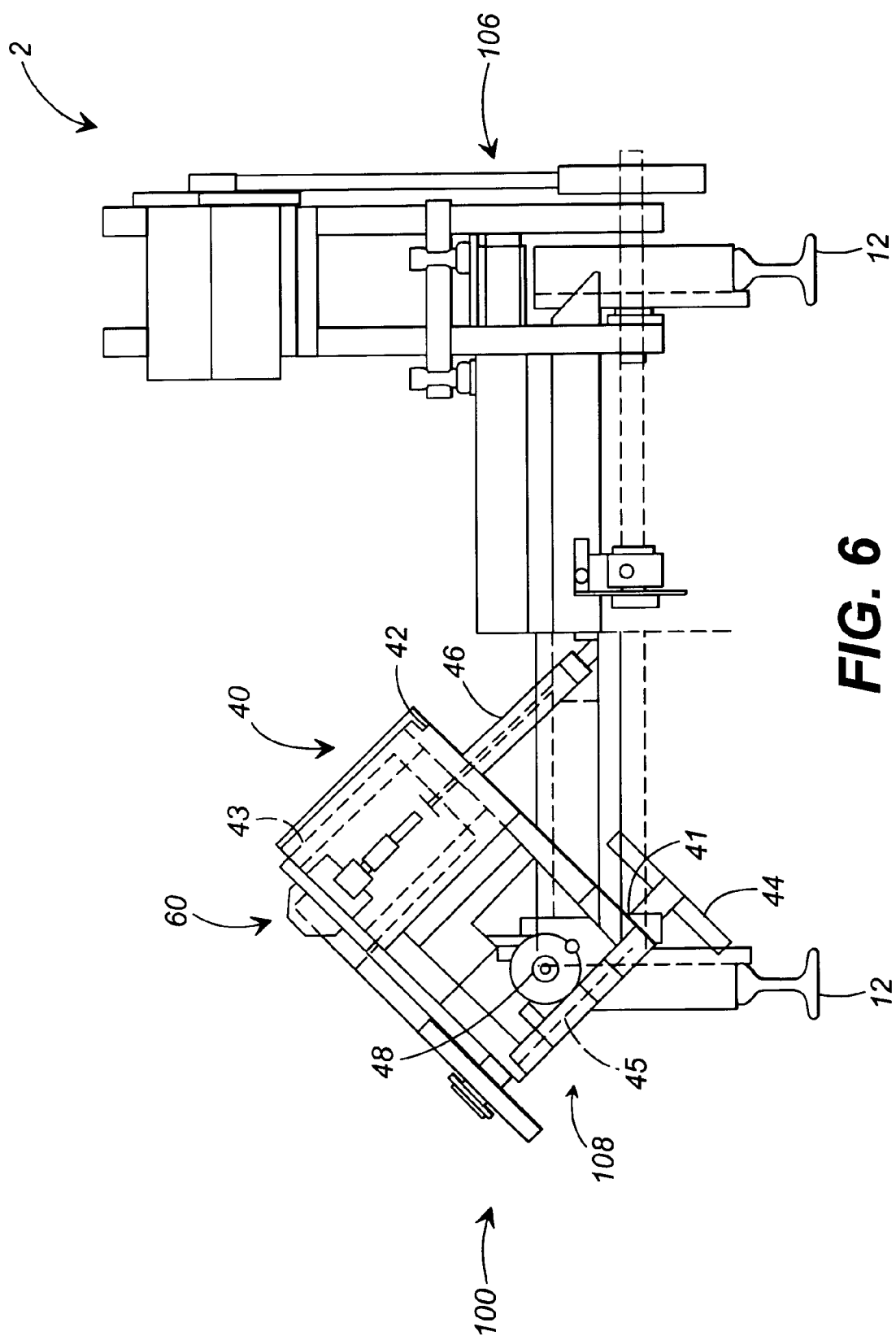
FIG. 6 is an end view of FIG. 5 with cut-away of gauge test wheel.

Generally similar to the tread test assembly 50, located forward the assembly 50, the gauge test assembly 40 comprises gauge test axle 41, gauge test frame 42, gauge testing wheel 44 and extension means 46. As shown in FIGS. 6 and 7, both the upper end 43 and the lower end 45 of gauge test frame 42 are both vertically and horizontally extendible, in opposite directions, from test cart 100 by an angled extension means 46 about pivot 48. Unlike the extension means 56 of the tread test assembly 50, extension means 46 imparts both vertical and horizontal displacement to urge the gauge testing wheel 44 toward the gauge surface 16 of rail 12, and ultimately to engage the gauge testing wheel 44 to the gauge face 16 of rail 12.

The application of vertical forces through the extension means 56, and of vertical and horizontal forces through the extension mean 46, can also be accomplished through the use of other hydraulic or pneumatic systems, other than the preferred air cylinders 46, 56. Because of space and weight limitations of the tribometer 2, while hydraulic systems can be used, it was found that air produces a lower cost system, and further is readily available on most track vehicles 400.

As previously disclosed, there are various embodiments of rail test assemblies 40, 50. The test cart 100 can comprise a single rail test assembly, either a gauge test assembly 40 or a tread test assembly 50, comprising a single testing wheel 44 or 54, so that two passes of the tribometer 2 over the same length of track to be tested is required to test both gauge surfaces 16 or tread surfaces 14 of the two rails 12. In another embodiment of the present invention 2, the tribometer 2 can have both a gauge and tread test assembly 40, 50, wherein each of the test assemblies 40, 50 comprise a single rail test frame 42, 52, a single testing wheel 44, 54 each to test one gauge and one tread surface of the railroad rail 12, and a single extension means 46, 56.

In yet another embodiment of the test cart 100, each of the rail test assemblies 40, 50 can comprise a single rail test frame 42, 52, two testing wheels 44R, 44L, 54R, 54L, one each for the two similar surfaces of the two rails 12, and a single extension means 46, 56. In this embodiment, the tribometer 2 can test the two surfaces of each rail 12 during a single pass. Yet, it is preferable for an assembly 40, 50 to comprise only one testing wheel per extension means during testing. Although this requires two separate passes of the tribometer 2 over the same section of track, there may be varying amounts on lubrication of the separate surfaces of the separate rails that an identical load to the separate testing wheels would not discover. Alternatively, the test cart can comprise more than one of the rail test assemblies 40, 50, thus having two separate rail test assemblies 40, 40 and or 50, 50, each subassembly having a rail test frame, one testing wheel and one extension means.

FIG. 4 depicts the test cart 100 having no gauge test assembly 40, and a tread test assembly 50 comprising a single tread test assembly frame 52, a single tread testing wheel 54L, and a single extension means 56. FIG. 5 depicts the test cart 100 comprising a single gauge test assembly 40 in the non-testing mode, and a single tread test assembly 50 in the testing mode. Shown in FIG. 6, the gauge test assembly 40 is in the testing mode with gauge testing wheel 44 in contact with gauge surface 16 of rail 12. FIG. 7 shows the test cart 100 having a single gauge test assembly 40 and a single tread test assembly 50, both retracted from rail 12.

The braking means 60 of the test cart 100 is the force application that causes the testing wheels 44, 54 to slow to the point of impending slip, and at which time the braking is freed. The braking system 60 may cycle from ten to thirty times a minute or more. As shown in FIGS. 5, 7 and 8, the braking means 60 comprises a dynamic braking motor 62 and transmission means 64 to transmit the dynamic braking to the testing wheel 54. The tread test assembly 50 is used to illustrate braking means 60, which description equally applies to gauge test assembly 40. Both the braking motor 62 and transmission means 64 are supported by the tread test frame 52. The transmission means 64 can comprise belt 66 looping around the braking motor sprocket 67, and the driven sprocket 68 of the testing wheel 54. When tread test assembly 50 enters the testing mode, upon contact between testing wheel 54 and the rail 12, the rail 12 imparts rotational velocity upon the testing wheel 54 equal to that of the speed of the tribometer 2, or the speed of the cart wheels 34. Wheel 34L is the left side cart wheel and 34R is the right side cart wheel. Upon the application of dynamic braking, the transmission means 64 begins to slow the speed of the tread testing wheel 54 to below the speed of the cart wheels 34.

The present invention 2 can further comprise an attachment means 200 which releasably attaches the test cart 100 with a motive means, preferably a hi-rail vehicle 400. The present invention is designed so that a hi-rail vehicle 400 can push the test cart 100 down the track 12. As shown in FIG. 10, the test cart 100 is preferably releasably attached to the test cart 100 by attachment means 200 comprising a stiff arm 210 pivoting from the front 410 of vehicle 400 to the pivot point 220 extending from front end 102 of the test cart 100 at point 36. The attachment means 200 provides the longitudinal force of forward travel to the tribometer 2 without introducing unwanted horizontal or vertical forces. The push attachment configuration is preferable because the rubber tread of hi-rail vehicle wheels 420 typically alters the rail 12 lubrication conditions, thus making accurate COF measurements nearly impossible if the tribometer were pulled behind a vehicle 420. Further, the tribometer 2 is designed so that the operator of the hi-rail vehicle 400 is able to see the railroad track 12 and all flangeways at all times ahead of vehicle 400 and tribometer 2.

Additionally, the attachment means 200 allows the tribometer 2 to simply and easily connect and disconnect to, for example, either a hi-rail vehicle 400 or track geometry car. The attachment means 200 can be modified for permanent attachment to the underside of the vehicle, if preferred. In the case of the geometry car, the tribometer 2 can be in front of, underneath or be pulled behind the geometry car. Although, as described above, when using a hi-rail vehicle 400, the tribometer should be pushed in front of the vehicle 400.

Before and after releasably attaching the tribometer 2 to the push vehicle, the tribometer 2 can be loaded and unloaded to the track 12 from the bed of a hi-rail vehicle 400 via portable rails or ramps (not shown). Typically, the tribometer 2 is placed onto the rail 12 by two people or with the aid of a winch. Once the tribometer 2 is in place on the rail 12, the hi-rail vehicle 400, for example, eases forward until the attachment means 200 couples the vehicle 400 with the tribometer 2.

One of the several advantages of the present invention is that all control and measurement functions can be automated. Generally automated system 300 controls the test cart 100 and measures the COF and related data. In relation to the control of the test assemblies 40, 50, as shown in FIG. 11 preferably a load cell 310 is located between the extension means 46, 56 and the testing wheels 44, 54, which load cell controls and monitors the load applied to the surfaces 14, 16 of the rail 12 via the extension means 46, 56. A block diagram of the automated control systems 300 is provided in FIG. 12.

Figure 12:
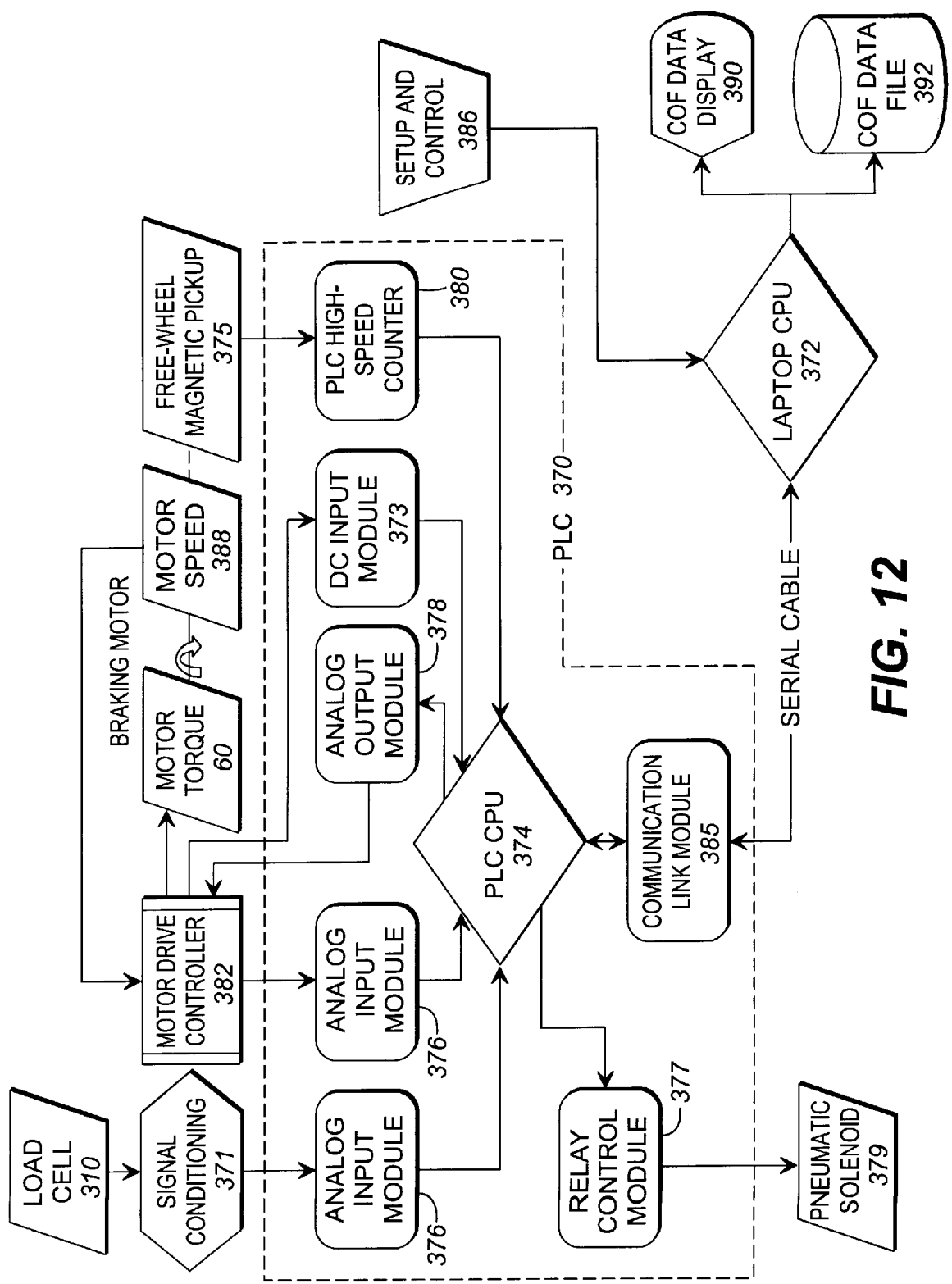
FIG. 12 is a block diagram of the control systems of a preferred embodiment of the present invention.

FIG. 12 is a block diagram of a preferred embodiment of the control system 300. As shown, two CPU's 370, 372 control this process. CPU 370 is a PLC, and the other CPU 372 is preferably a laptop PC. A keyboard 386 on the laptop 372 is the primary means for setup and control of the present process. The PLC 370 controls the data collection process. It receives data from four load cells 310 (the live load on each test wheel), the speed 380 of the two speed cart wheels 34 (test cart 100 speed on each rail 12), and the four motor 62 speeds 382 (speed of the test wheels 44, 54). Additionally, the PLC 370 commands the raising and lowering of the test wheels 44, 54 via the extension means 46, 56.

The PLC 370 consists of several modules. All modules are attached to a bus plane. A power supply module powers the bus plane. A CPU module 374 controls and communicates with all the modules. Control software is stored in the CPU 372.

A high-speed counter module 380 receives pulses from the free wheel magnetic pickup unit 375. This unit pulses each time a gear tooth passes it. The gear is attached to the free wheels 34. The speed of the test wheels is monitored by an internal speed encoder 388 in the braking motor 62. The analog input modules 376 convert analog signals to digital signals. One module provides the load on each test wheel with signals received from the load cells 310, which are amplified and filtered by the signal conditioning unit 371. The other module converts signals sent from the motor drive controller 382. These signals monitor the drive system and alert the operator should a system fault occur.

The analog output module 378 converts digital signals from the CPU to analog signals. These signals control the motor drive controller 382. The DC input module 373 detects the presence of signal voltage, and is used to monitor the functions of the motor drive controller 382. The relay control module 377 sends power to the pneumatic solenoids 379 which control the air cylinders applying the load to the test wheels. The communication link module 385 provides a serial network connection with the laptop CPU 372. This allows the laptop to control the PLC CPU 374 for setup and data collection.

The PLC 370 first starts the test cycle, then commands the torque 62 applied by the motor drive controller 382 to each test wheel and then compares the reference wheel speed to the test wheel speed. When the test wheel slows to a preset speed differential, the PLC sends the torque value and load cell value to the PC. This cycle is repeated every 2 seconds ending with data sent to the PC 372. The COF tread test and COF gauge test are preferably performed one second apart.

The PC 372 controls the PLC 370. The PC 372 commands the PLC 370 to: raise and lower the testing wheels; start and stop testing; and transmit data used for calibration. The PC 372 then processes the test data and displays the COF and other parameters on a monitor 390 for a real time display of the testing in progress. Data is stored on a hard drive 392 of the PC 372 in a comma delineated ASCII file.

The automated systems 300 further address the need for both the control of force and stroke amount to the extension means 56. The effects of inertia on the test assemblies 40, 50 are also filtered out by systems 300.

The automated systems 300 also control the power supplied to the present invention 2. The tribometer 2 preferably draws power from the host vehicle 400 at whatever voltage the host vehicle 400 provides. In one test run, a host vehicle 400 carried a 230/120 volt ac generator to power (excite) the servo motors. A control cabinet, not shown, can provide all other voltage required. The host vehicle also carried the air supply for the system. Typically, control systems 300 will rely on approximately 12V D.C. as supplied by the host vehicle 400. Alternatively, the present invention can be powered by on-board energy sources, which can include batteries 320 and solar cells 322 as shown in FIG. 13. Many embodiments of the present invention are capable of operating continuously for up to twelve hours, and be rechargeable in six hours from 110V AC.

Control over the dynamic braking means 60, and measurements thereof, are used in determining the COF measurements. The braking is preferably applied by a ramp. If a test wheel 54 were to slip in relationship to a cart wheel 34, the braking effort would then exceed the COF of the rail 12. Therefore, the braking must be released prior to slip to prevent the test wheel 54 from locking-up and sliding down the rail 12.

The measurement systems 300 measure the effective lubrication/coefficient of friction on both rails 12, for either or both the tread 14 and gauge 16 surfaces of each rail 12. Measurements taken include, but are not limited to the: a) calculated coefficient of friction (COF) at discrete measuring points, b) distance from initial location down the track or landmarks, and c) critical components making up the coefficient of friction calculation, such as applied forces in each direction, etc. Further, an odometer can be included in automated systems 300 so that the measurements can be indexed to mileposts or other convenient reference locations. Other measurements include track curvature and track gauge.

It should be noted that different COF values are required for tangent (straight) track vs. curved track. As shown in FIG. 14, tangent track is a length of railroad track that has a straight alignment. Curved track is a length of track that has a continuous change in the same direction. A simple curve has the same rate of change throughout its length. The report of COF for track must differentiate between these two. The purpose of a curve detector is to separate the test data between tangent track and curved track. Curved track can be further delineated by its severity.

To measure track curvature, a linear variable differential transformer (LVDT) can be used. An LVDT is a device that produces a specific voltage in relationship to the position of its armature. The voltage output is generally zero at its retracted position and maximum at its most extended position. The voltage change between these positions is linear. Therefore, this device can be used to accurately indicate its position. When this device is attached to a mechanism with the transformer attached to the stationary part, and the armature attached to the moving part, the distance between the parts can be accurately measured. LVDTs generally can provide a reliable and accurate means of measuring displacement and position over a range from a few microns to 25 mm.

As shown in FIGS. 15a and 15b, an LVDT 600 can comprise a primary winding 610, two identical secondary windings 620 on a common bobbin and a moveable magnetic core or armature 630. The primary winding 610 is excited with an ac supply. The two secondary windings 620 are connected so that their combined output represents the difference in the voltage induced into them. With an armature 630 in the central position, the output is zero. Movement of the armature 630 from this position produces an output that is proportional in phase and magnitude to the armature 620 displacement.

Preferably, an LVDT is mounted between the attachment means from a truck 400 to the test cart 100. As the cart 100 and truck 400 move around a curve, the distance between the cord and the test cart 100 will change. The degree of change is proportional to the severity of the track curvature as seen by this cord offset. Various voltages from the LVDT indicate the track curvature.

The operator may have to recalibrate the synchronization between the testing wheels 44, 54 and the cart wheels 24, 34 before each test. Typically re-calibration is not necessary. The PLC on board monitors the wheel speeds and notifies the operator if re-calibration is necessary.

Since the point of creepage is a critical value in the measurement systems' 300 COF calculations, it is necessary for accurate results to have all the wheels travel at the same relative speed. The COF measurements preferably are a rolling average value of the last four COF measurements made. Measurements are taken generally every 2 second; therefore, at 30 mph, readings are made every 88 feet. Alternately tread and gauge measurements are taken one second apart. It should be noted that the AAR specification for COF testing frequency is every 50 to 100 feet.

The measurement systems 300 also record the computed braking torque on the testing wheels 44, 54, and the load on the testing wheels 44, 54 at the point of slip detection This data is used to compute the COF of the rail 12 at that point. The control systems 300 stop the application of the braking torque upon the detection of slip, and resets the system for the next test. Slip percentage, or the value of the difference between the speed of the cart wheels 24, 34 and the testing wheels 44, 54 is typically in the range of between 1–20%, with 12% as the default for gauge and 18% for tread.

The operator also inputs the COF limit, which is the maximum value of torque that will be generated by the braking means 60. Preferably, the default is 0.5 (50%) of maximum braking torque.

The measurement systems 300 preferably also determine the location of the tribometer 2 from the right rear reference wheel 34R by a pulse count output. The systems 300 can comprise a 160-tooth gear on a 16-inch diameter cart wheel 34, generating one count for each 0.314 inches of travel. The constant used as a default in this configuration is 201,681.14 counts per mile. Thus, the speed of the tribometer 2 is automatically calculated by the following formula 1:

$$\text{Speed} = \text{Distance}/\text{time} \tag{1}$$

Where:
Speed=Counts per 500 ms (update speed each 500 ms); and
MPH=number of counts÷28.01126.

For data collection, the tribometer 2 provides computerized collection of the information for processing and transfer, and can also include a hard copy. As shown in FIG. 12, preferably an RS232 connection provides an interface to a portable device to download the data. The portable device can have a modem for electronic transfer of data. Another tethered, rugged device (not shown) can provide a display of the following functions at any time during the test:

a. coefficient of friction at each location
b. date/time
c. distance
d. applied forces (average over some predetermined distance and/or time)
e. battery time remaining (if applicable)

The tethered device enables the operator to check real-time data without waiting for the download. The tethered device can also have buttons to start and stop data collection and mark the record for special notations.

Prototype Testing

Working prototypes of the entire tribometer of the present invention, and of the several elements thereof, were tested for workability. The following descriptions are examples of tested embodiments. The braking torque can be applied by use of a permanent magnetic brushless motor. The magnets spinning in the motor generate an electric current. When an electric load is placed in the current's path, an electromotive force is generated against the magnets, inhibiting the motor from turning. This electromotive force generates a torque that resists the turning of the motor shaft. By controlling the electromotive force, a specific torque can be produced. Thus, the braking means can comprise a motor (acting as a generator); a control device for varying the current applied to a load; a regenerating resistor; and a power supply to excite the motor/generator, and to power the control system.

Figure 9:
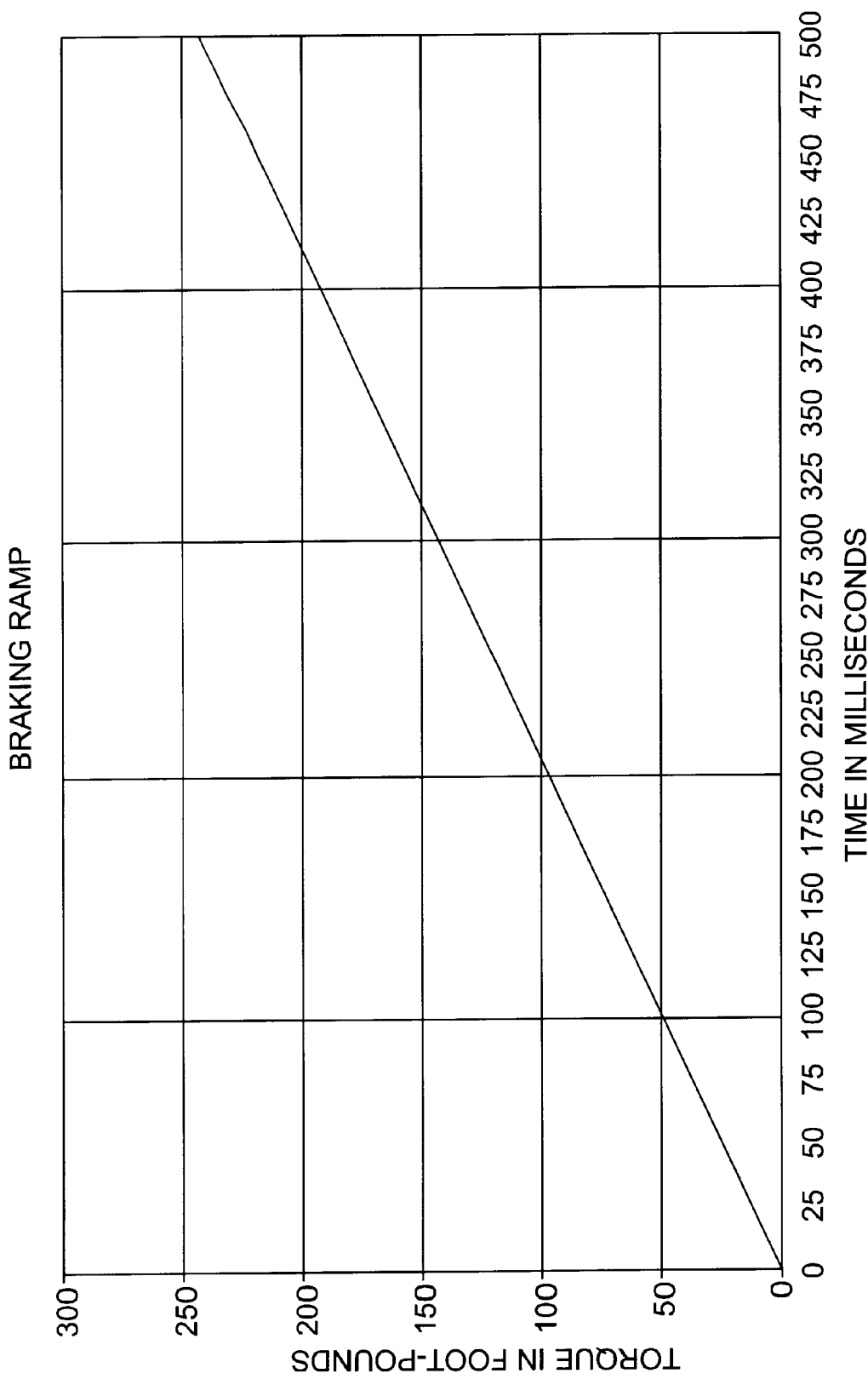
FIG. 9 is a graph of torque vs. time in reference to one embodiment of the braking means of the present invention.

In one prototype, the motor had a known maximum braking force of 242.5 ft-lbs. The control system can apply a braking ramp by signaling the motor control to apply a specific electromotive force. As shown in FIG. 9, by linearly increasing the braking torque, and monitoring the test wheel velocity to a reference wheel traveling on the same surface, the point when the velocities are different can be found. The braking force at that point can be used to determine the COF.

The braking was applied by a ramp with the preferable length of the ramp 500 ms, and the height of the ramp generally 250 ft-lbs. The step value which was incrementally added to the brake control approximately every 2 ms was entered by the operator. In that there are approximately 250 scans per test, an increment value of 4 would approximately reach 50% of maximum braking torque in 500 ms.

In reference to the default value for a COF limit, a PLC torque control value of 840 was chosen. This value equaled a braking torque of 124 ft-lbs. The ramp rate therefore was set for 248 ft-lbs. (8 volt command to the KM servo control, PLC value of 1680). This was required so that the regeneration resistor system was not overloaded. There is no value in obtaining COF readings over 0.5 because values over 0.5 indicate the rail has no lubrication present.

Generally, the operator also inputs the braking ramp rate. This is the PLC value for each 2-millisecond step. The ramp is preferably 500 milliseconds long, and the value of the COF limit set high. A value of 3 would equal 750 at the end of 500 milliseconds.

The automated systems 300 also controls and measures the load on each test wheel 44, 54. The air pressure in each loading cylinder 46, 56 (the preferable extension means) must be adjusted to produce the correct amount of pre-load (approximately 250 lbs. on the gauge surface 16, and 350 lbs. on the tread surface 14 of the rail 12 in a prototype run). These loads are applied through the cylinders 46, 56, which themselves produce an offset factor. This offset factor must be adjusted as various components are changed on the tribometer 2. Maintaining and measuring the pre-load is essential in obtaining accurate values used in determining the COF for each tested surface.

The tribometer is preferably made of high strength materials capable of handing the loads and abuse of a railroad environment. When the tribometer 2 travels at 30 MPH, these loads are extreme. A prototype was tested with a 16-inch test wheel, which was selected for two reasons: to keep the speed of testing wheels and the cart wheels the same, and 16-inch railroad cart wheels were easy to obtain.

Because steel 16-inch rail wheels are heavy, the tribometer used to support these wheels must also be heavy, resulting in a heavy dead weight applied to the rail. Because the testing wheels travel along a relatively uneven rail (±0.045 inches), the inertial effects of the wheel can cause rail surface unloading. Therefore, in this prototype a suspension system was needed to keep rail loading as constant as possible.

The load of the wheels was established by putting as much weight on the rails as possible using the following restraints: 1) the weight transferred to the testing wheels must not unload the rear axle, which would increase the possibility of derailment; 2) the weight applied by the suspension system and measured with the load cells must be within the limits of the load cell capacity for the accuracy range required; and 3) the load applied to the gauge face of the rail must not cause the testing wheel, which rides high on the gauge corner, to derail during normal cart dynamics.

These loads were selected based on the inventor's experience, and verified with field-testing. Additionally, the AAR/TTC used a NUCARS computer model to verify the tracking capacity of this prototype. Based on AAR's evaluation, the design was modified to overcome identified problems.

The AAR/TTC specification stated that the speed of testing should be up to 35 mph. The motor/generator and gearing selection using "off-the-shelf" components provided for testing speeds up to 30 mph (accepting operating at 33 mph without damage to components). As a practical matter, operators are very uneasy driving hi-rail vehicles at speeds greater than 30 mph.

The specified sampling rate required that the measurements be taken every 50 to 100 feet. One prototype used a time-based system, which takes measurements every 88 feet at 30 mph. Based on the physical characteristics of the prototype, the "sweet-spot" for testing was between 15 and 20 mph. At this speed range, the tribometer obtained readings that more closely match those of the existing hand held tribometer. The prototype system used an inertia correction factor to enlarge this "sweet-spot" to between 10 and 25 mph.

Measurements were averaged using a trailing average of the last four measurements. At speeds over 25 mph, the data values were outside the ability to capture due to the upper limit of the transducers. At speeds less than 10 mph, the dynamics of the components selected produced data with a lower value then shown by the hand held tribometer.

The Preferred Tribometer Computational Process

As described, one of the purposes of the tribometer 2 is to measure the coefficient of friction on the tread 14 and gauge 16 surfaces of the railroad rail 12. This process is performed periodically as the apparatus 2 rides along the rail 12 at various speeds. The coefficient of friction as used herein is defined as the ratio of drag over load. For example, in reference to tread test assembly 50, load is the applied weight of the testing wheel 54, and drag is the force resisting the rotation of the testing wheel 54. Load is applied on the testing wheel 54 by two means. The first is the static weight of the wheel 54 and the supporting framework 52, which is called the dead weight ($W_{Dead}$). The second is the load applied with the extension means 56, which is the dynamic weight ($W_{Dynamic}$).

Figure 16:
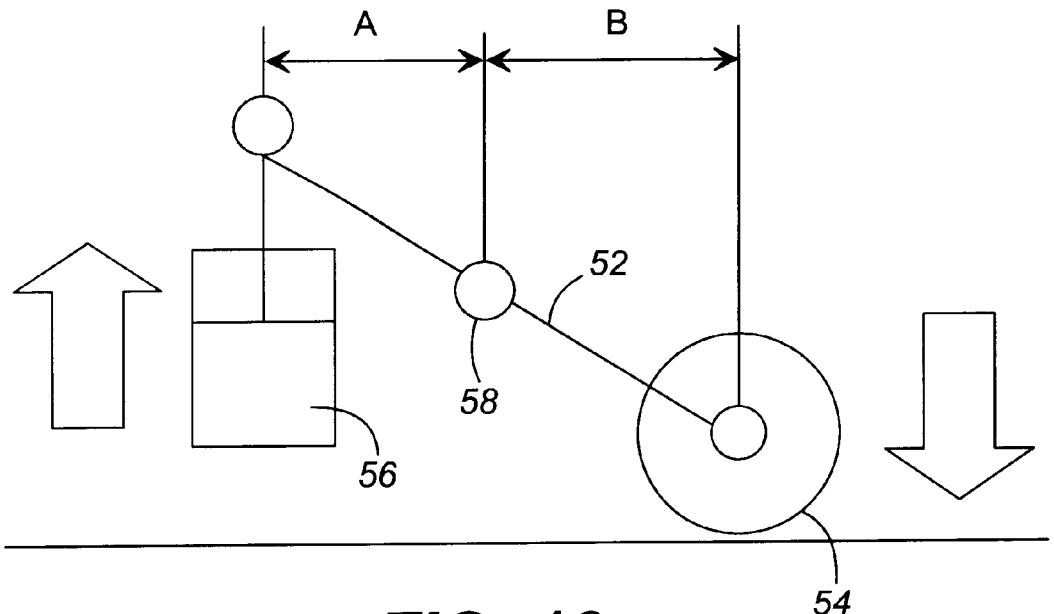
FIG. 16 is an illustration of the dynamic weight of the tread test assembly of the present invention.

As shown in FIG. 16, the extension mean's 56 force is applied to the test cart 52 at the opposite end from the testing wheel 54. The ratio of the distance (A) between the cylinder 56 end and the pivot 58 to the distance (B) between the testing wheel 54 and the pivot 58 is called the mechanical multiplier (MP). The load cell 310 measures the load ($W_{Dynamic}$) applied by the cylinder 56. The total load ($W_{Load\ Total}$) is computed by formula 2:

$$W_{Load\ Total} = (W_{Dynamic}) \times (MP) + W_{Dead} \tag{2}$$

As for drag, there is a negligible amount of drag caused in the present invention 2 by the transmission means 64 and therefore, this is ignored in the calculations. The dynamic braking motor 62 creates drag. Braking is sequentially increased in steps by a specific increment of torque. The speed of the testing wheel 54 is compared to the speed of the cart wheels 34, which always rotate freely. When the testing wheel 54 reaches a specified speed below that of the cart wheels 34, the testing wheel 54 is considered sliding. This is the point where the maximum amount of driving force can be transmitted from the rail 12 to the testing wheel 54. The force transmitted is directly proportional to the COF for the rail 12 surface.

Formula 3 is used to determine drag:

$$\text{Drag} = \text{Force}_{Torque} - \text{Force}_{unload} - I_{wheel} \quad (3)$$

Where:

Applied Torque (Force$_{Torque}$) is the force generated by the braking motor 62 at the rail 12/testing wheel 54 interface;

Unload (Force$_{unload}$) force is generated by the geometry of the testing wheel 54 as related to the test cart 100; and Wheel inertia (I$_{wheel}$) is dependent on the rotational velocity of the testing wheel 54 and its mass.

The unload force is only generated by the tread testing wheel 54. Applied Torque (Force$_{Torque}$) is determined by formula 4:

$$\text{Force}_{Torque} = (SV/MSV)(MT)(WR) \quad (4)$$

Where:

SV is the step value as commanded by the PLC;

MSV is the maximum step value that can be issued by the PLC;

MT is the maximum foot-pounds of torque that can be delivered by the braking motor 62; and WR is the testing wheel's 54 radius in feet.

Figure 17:
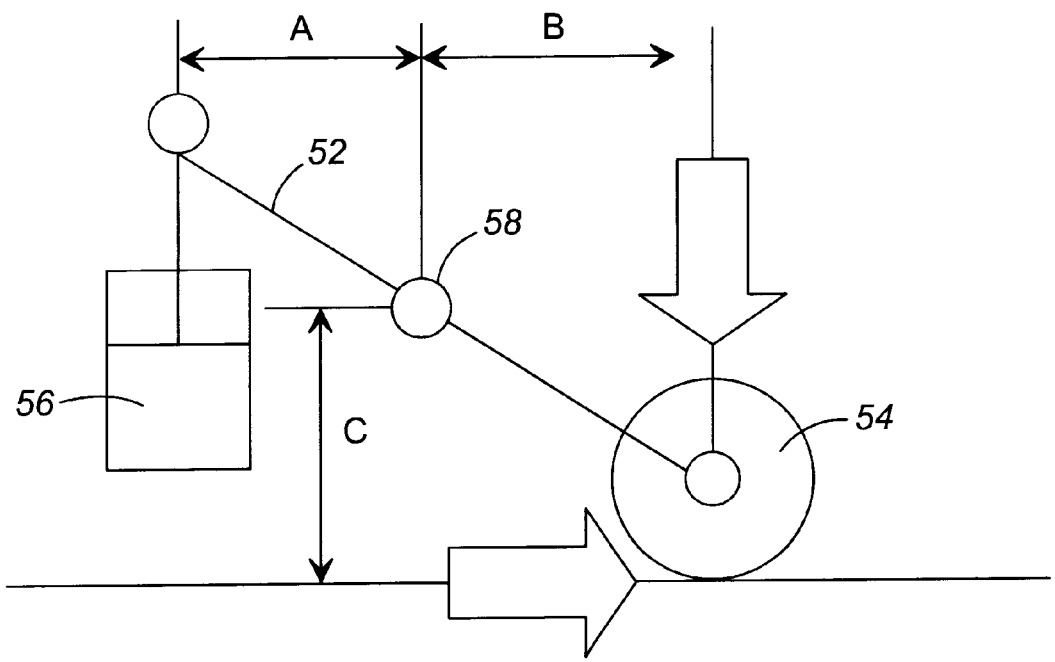
FIG. 17 is an illustration of the unload force of the tread test assembly of the present invention.

The Unload Force (Force$_{unload}$) is illustrated in FIG. 17, and is determined by formula 5:

$$\text{Force}_{unload} = \text{Force}_{Torque} (B/C) \quad (5)$$

Where:

B is the horizontal distance from the pivot point 58 to the center of the testing wheel 54; and C is the vertical distance from the pivot point 58 to the top of the rail 12.

To correct for inertia in the measured COF (COF$_M$), the following calculations should be computed. The time difference ($\Delta_t$) between actual slip point and the additional time to reduce the test wheel velocity by a selectable difference, for example, 18% and 12%, is determined by formula 6:

$$\Delta_t = \sqrt{\frac{2 \times K_e}{B_R}} \quad (6)$$

Where:

K$_e$=Difference between kinetic energy from the initial velocity of the test wheel and the kinetic energy in the test wheel after an 18% reduction in velocity; and B$_R$=Braking rate in foot-pounds per millisecond.

Kinetic energy (K$_e$) is determined by formula 7:

$$K_e = (0.5 \times S_I \times S_{v1}^2) - (0.5 \times S_I \times S_{v2}^2) \quad (7)$$

Where:

S$_I$=System inertia in foot-pounds per second squared;

S$_{v1}$=System velocity at start of test; and

S$_{v2}$=System velocity a slip detection (18% or 12%).

Therefore, the measured coefficient of friction (COF$_M$) must be corrected by subtracting the torque (COF$_I$) required to slow the test system by 18% or 12%, which torque is defined as:

$$COF_I = \frac{\Delta t \times B_R \div 0.667}{W_{LoadTotal}} \quad (8)$$

Where:

W$_{Load\ Total}$=Weight of the test wheel on the rail.

Thus, the actual COF is equal to the COF measured (COF$_M$) minus the torque (COF$_I$):

$$COF = COF_M - COF_I \quad (9)$$

The above provides a straight-line relationship between inertial COF correction and velocity. A rate of correction based on the speed of the test cart may be subtracted from the measured COF.

Test Results of a Prototype

A prototype tested the dynamic analysis of the effects of the tribometer 2 on the testing wheels 44, 54, and the testing wheels' 44, 54 effect on the tribometer 2. The effect of the test cart 100 being pushed by a vehicle 400 was also tested. As a result, the following was found: the testing wheels' 44, 54 surface contact line moved smoothly as a result of rail curving; that proper testing wheels 44, 54 braking occurred; and that gauge surface 16 hunting was successful. It was also found that the cart wheels 24, 34 and the testing wheels 44, 54 tracked the surfaces 14, 16 of the rail 12, and that the range of wheel force variation worked well in the analysis as the tribometer 2 might expect to see in the field, based on rail surface 14, 16 variations. The above data was accurate at the various speeds the present invention 2 operates, namely 10–35 mph.

For the analysis, it was estimated that the following information would be utilized. The test cart's 100 weight distribution was as shown in Table 1:

TABLE 1

Tribometer Weight and Balance

| Item | Station | Weight | Moment | Front | Rear |
|---|---|---|---|---|---|
| Front Axle | 0 | 1282 | — | 1282.00 | 0.00 |
| Rear Axle | 72 | 2171 | 156,312 | 0.00 | 2171.00 |
| Center Jack | 46.25 | 300 | 13,875 | 107.29 | 192.71 |
| Total | | 3753 | 170,187 | 1389.29 | 2363.71 |
| CG | | | | 45.35 | (26.65) |

Figure 18:
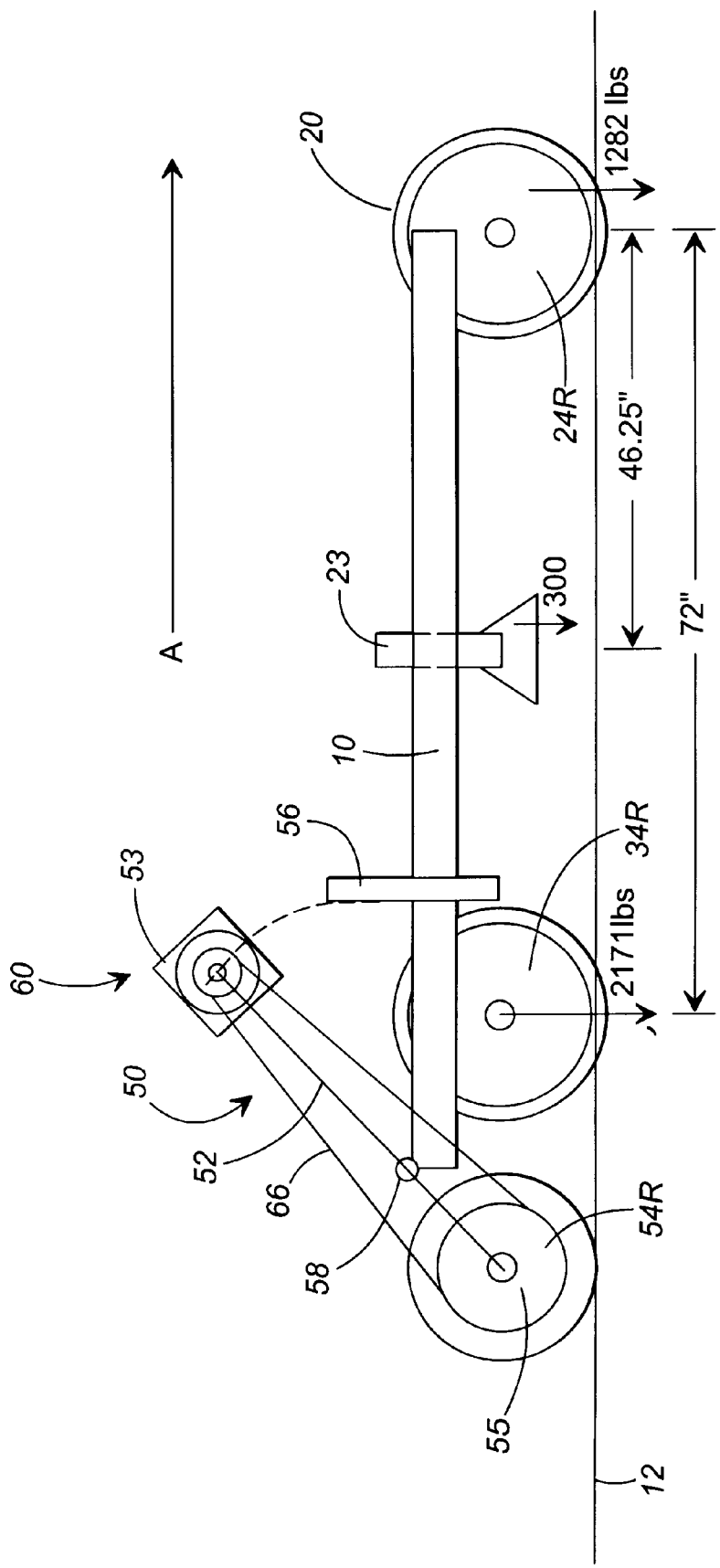
FIG. 18 is FIG. 4 with referenced dimensions and weight distribution according to a preferred embodiment of the present invention.

As illustrated in FIG. 18, the 0 station (stations which are of measurements of inches of length from the front axle 22) refers to the front axle 22, weighing 1282 pounds. The weight on the rear axle 32 on the prototype was 2171 lbs. A center jack 23 was available to raise and pivot the tribometer about its center point. This allowed the machine, which can test in only one direction, to be rotated 180 degrees at any road crossing to test in the opposite direction. Additionally, the tribometer can be rotated 90 degrees at a road crossing to be removed from the track at right angles.

In reference to the effect of the braking means 60 applying a cyclical braking force on each testing wheel 44, 54, it was possible that such a braking force can cause a tracking problem on the test cart 100. Therefore, the prototype applied a ramped up brake load on the two tread test wheels 54R, 54L simultaneously. However, if when one wheel 54 started to slip, only that wheel 54 would be de-braked. During testing, the test cart 100 could reach a COF of approximately 0.5 on one testing wheel 54 while the other testing wheel 54 could be approximately 0.2. The rate of sampling for the running surfaces 14 of the two rails 12 was every 2 seconds. The gauge test assembly 40 worked in a similar fashion, with a delay of 1 second.

The tread assembly weight and balance assembly 50 was as follows:

TABLE 2

Tread Assembly Weight and Balance

| Item | Description | Unit Weight | Number | Part Weight | Station | Moment inch-lbs. |
|---|---|---|---|---|---|---|
| 1 | Test wheel & axle | 44.90 | 1 | 44.90 | 15.38 | 690 |
| 2 | Structural tube | 1.91 | 1 | 1.91 | −19.11 | −36 |
| 3 | Structural tube | 2.89 | 1 | 2.89 | 15.38 | 44 |
| 4 | Structural tube | 23.54 | 2 | 47.08 | 1.29 | 61 |
| 5 | Structural tube | 2.98 | 1 | 2.98 | 10.96 | 33 |
| 6 | Wheel bearings | 6.65 | 2 | 13.30 | 15.38 | 205 |
| 6 | Wheel bearings | 6.65 | 2 | 13.30 | 0.00 | 0 |
| 7 | Wheel sprocket | 21.7 | 1 | 21.70 | 15.38 | 43 |
| 8 | Motor sprocket | 2.8 | 1 | 2.80 | −0.53 | −1 |
| 9 | Belt | 2 | 1 | 2.00 | | 0 |
| 10 | Motor adj. Plate | 9.44 | 1 | 9.44 | −10.11 | −95 |
| 11 | Motor base | 20.08 | 1 | 20.08 | −4.60 | −92 |
| 12 | Plate | 3.83 | 2 | 7.66 | 17.14 | 131 |
| 12 | Plate | 3.83 | 2 | 7.66 | 1.77 | 14 |
| | Cylinder applied load* | −250.00 | 1 | −250.00 | −17.13 | 4283 |
| 13 | Motor foot | 34.61 | 1 | 34.61 | −3.28 | −114 |
| 14 | Motor | 79.00 | 1 | 79.00 | −0.53 | −42 |
| | | | | 61.31 | | 5122.31 |
| | Force on Rail | 333.05 | | | 15.38 | |

* Cylinder Forces Required Applied F Psi
Wheel loaded       250       79.592
Wheel pickup       160       56.537
Cap area = 3.141 sq. in.
Rod area = 2.83 sq. in.
Note: without belt guard The item numbers referred to in Table 2 were distinct parts of the prototype assembly as tested. As disclosed and referenced herein, items 2–5 would relate to the test frame assembly 50; items 1, 6, 7, and 12—the test wheel assembly 54; items 6 and 12—the pivot assembly 58; items 8, 10, 11, 13 and 14—the motor assembly 60, and item 66—the belt 60.

The load on the rail 12 applied by the testing wheel 54 was 333 lbs. In order to control the weight of the testing wheel 54 and be able to remove it from the rail 12 tread surface 14, this part of the test assembly 50 was counterbalanced. The load applied to the rail 12 tread surface 14 was a combination of the unbalanced load and additional load applied by the air cylinder 56.

While the invention has been disclosed in preferred forms, it will be apparent to those skilled in the art that many modifications, additions, and deletions can be made therein without departing from the spirit and scope of the invention as set forth in the following claims.

What is claimed is:

1. An apparatus for measuring the coefficient of friction of a surface of a rail of a railroad track, comprising:

(a) a test cart capable of riding the rails of the railroad track;

(b) at least one rail test assembly attached to said test cart, said at least one rail test assembly having a rail testing wheel, wherein said rail test assembly is capable of moving between a testing mode and a non-testing mode, said rail test assembly in the testing mode capable of placing said rail testing wheel into communication with the rail surface to be tested, said rail test assembly in the non-testing mode capable of removing said rail testing wheel from communication with the rail surface; and (c) a braking system to brake said rail testing wheel while in communication with the rail surface to be tested.

2. The apparatus of claim 1, wherein said at least one rail test assembly further comprises:

(a) a rail test frame having an upper end and a lower end;

(b) a rail test axle assembly at the lower end of said rail test frame, wherein said rail test axle assembly provides said rail testing wheel free rotation upon contact with the rail to be tested; and (c) an extender which, during the testing mode of said rail test assembly, urges said rail testing wheel towards the rail to be tested, and during the non-testing mode, retracts said rail testing wheel from the rail.

3. The apparatus of claim 2, farther comprising an attachment device to attach said apparatus to a vehicle, which vehicle provides the apparatus with movement down the railroad track.

4. The apparatus of claim 3, wherein said braking system provides dynamic braking to said rail testing wheel until said rail testing wheel reaches the point of creepage, at which point said braking system is released.

5. The apparatus of claim 4, said test cart capable of riding the rails of the railroad track by a front axle having front cart wheels and a rear axle having rear cart wheels, wherein said front axle of said test cart can rotate about the longitudinal center line of said test cart; and wherein said rear axle is split, providing each said rear cart wheel rotation independent from the other.

6. The apparatus of claim 5, wherein said rail test frame of said at least one rail test assembly is pivotally connected to said test cart at generally the mid-point of said rail test frame.

7. The apparatus of claim 6, wherein said at least one rail test assembly comprises at least one tread test assembly to test the tread surface of a rail.

8. The apparatus of claim 6, wherein said at least one rail test assembly comprises at least one gauge test assembly to test the gauge surface of a rail.

9. The apparatus of claim 6, wherein said at least one rail test assembly comprises at least one tread test assembly and at least one gauge test assembly.

10. The apparatus of claim 9, wherein said extender of said rail test assemblies comprises an air cylinder, said cylinder attached at one end to the upper end of said rail test frame, and at the other end to said test cart.

11. The apparatus of claim 10, wherein said attachment device comprises a stiff arm pivoting from the vehicle to an attachment pivot point on said test cart.

12. The apparatus of claim 11, wherein the operating speed of the apparatus is approximately 10 to 35 mph.

13. A tribometer for testing the efficiency of lubrication upon a railroad rail surface, said tribometer comprising:
(a) a test cart that rides the railroad track to be tested, and tests the coefficient of friction of a surface of a rail of the track, said test cart including a test cart frame, front and rear axle assemblies supporting said test cart above the railroad track, each said axle assembly having an axle and two cart wheels, said front axle being capable of rotation about a longitudinal center line of said test cart frame, said rear axle being split, providing each said rear cart wheel rotation independent from the other, and at least one rail test assembly to test the rail's surface conditions, wherein said rail test assembly is attached to said test cart frame, and has a testing mode and a non-testing mode;
(b) a motive means to move said test cart along the path of the railroad track to be tested, said motive means including an attachment assembly that attaches the tribometer to a vehicle, which vehicle provides movement to the tribometer down the railroad track; and
(c) automated systems to both control said test cart, and measure and record various data relating to both the speed and location of the tribometer, and the tested track's surface conditions.

14. The apparatus of claim 13, wherein the operating speed of the apparatus is approximately 10 to 35 mph.

15. The tribometer of claim 14, wherein said at least one rail test assembly comprises:
(a) at least one tread test assembly to test the tread surface of a rail; and
(b) at least one gauge test assembly to test the gauge surface of a rail.

16. The tribometer of claim 15, wherein the tread test assembly comprises:
(a) a tread test frame having an upper end and a lower end;
(b) a tread testing wheel;
(c) a tread test axle assembly at the lower end of said tread test frame securing said tread testing wheel to said tread test assembly, while providing said tread testing wheel free rotation about said tread test axle; and
(d) an extension means which, during the testing mode of said tread rail test assembly, urges said tread testing wheel towards the tread surface of the rail to be tested, and during the non-testing mode, retracts said tread testing wheel from the tread surface of the rail.

17. The tribometer of claim 16, wherein the gauge test assembly comprises:
(a) a gauge test frame having an upper end and a lower end;
(b) a gauge testing wheel;
(c) a gauge test axle assembly at the lower end of said gauge test frame securing said gauge testing wheel to said gauge test assembly, while providing said gauge testing wheel free rotation about said gauge test axle; and
(d) an extension means which, during the testing mode of said gauge rail test assembly, urges said gauge testing wheel towards the gauge surface of the rail to be tested, and during the non-testing mode, retracts said gauge testing wheel from the gauge surface of the rail.

18. The tribometer of claim 17, wherein said test frame is pivotally connected to said test cart frame at generally the mid-point of said test frame; and
wherein said extension means of said at least one tread and gauge test assembly comprises an air cylinder, said cylinder attached at one end to the upper end of said test frame, and at the other end to said test cart frame.

19. The tribometer of claim 18, said test cart further comprising a braking system that is capable of providing dynamic braking to at least one of said tread and gauge testing wheels until at least one of said tread and gauge testing wheels reach the point of creepage, at which point said braking system is released.

20. The tribometer of claim 13, said motive means being entirely located on said test cart, said motive means capable of moving the tribometer down the railroad track.

21. The tribometer of claim 13, a portion of said automated systems being remote from the tribometer.

22. A tribometer for testing the efficiency of lubrication upon a railroad rail surface of a railroad track, said tribometer comprising:
(a) a test cart being capable of riding the rails of the railroad track and testing the coefficient of friction of a railroad rail surface of the railroad track, said test cart including (i) a test cart frame supported by the railroad track, (ii) at least one rail test assembly having a rail testing wheel, said at least one rail test assembly being capable of movement between a testing mode and a non-testing mode, said at least one rail test assembly in the testing mode placing said rail testing wheel in communication with the railroad rail surface, and said at least one rail test assembly in the non-testing mode removing said rail testing wheel from communication with the railroad rail surface, and (iii) a braking system capable of braking said rail testing wheel during the testing mode of the at least one rail test assembly;
(b) a motive system capable of moving said test cart along the railroad track; and
(c) automated systems capable of both controlling said braking system, and measuring and recording various data relating to speed and location of said tribometer, and conditions of the railroad rail surface.

23. The tribometer of claim 22, said at least one rail test assembly further comprising:
(a) a rail test frame having an upper end and a lower end;
(b) a rail test axle assembly at the lower end of said rail test frame, said rail test axle assembly capable of providing said rail testing wheel free rotation upon communication with the railroad rail surface; and
(c) an extension device that is capable of both urging said rail testing wheel towards the railroad rail surface prior to the testing mode, and retracting said rail testing wheel from the railroad rail surface, initiating the non-testing mode.

24. The tribometer of claim 22, said motive system being located on said test cart and being capable of moving the tribometer down the railroad track.

25. The tribometer of claim 24, said motive system comprising an engine capable of supplying movement to at least one of said front and rear axle assemblies.

26. The tribometer of claim 22, said motive system comprising an attachment and a vehicle remote from the tribometer, the vehicle capable of providing movement to the tribometer via the attachment.

27. The tribometer of claim 22, said braking system of said test cart capable of providing dynamic braking to said rail testing wheel.

28. The tribometer of claim 27, said braking system of said test cart capable of providing dynamic braking to said rail testing wheel until said rail testing wheel reaches the point of creepage, at which point said braking system releases.

29. The tribometer of claim 22, said at least one rail test assembly having at least one tread test subassembly capable of testing the tread surface of the railroad track.

30. The tribometer of claim 22, said at least one rail test assembly having at least one gauge test subassembly capable of testing the gauge surface of the railroad track.

31. The tribometer of claim 22, said at least one rail test assembly having at least one tread test subassembly and at least one gauge test subassembly capable of testing the gauge surface of the railroad track.

32. The tribometer of claim 22, a portion of said automated systems being remote from the tribometer.

33. A tribometer for testing the efficiency of lubrication upon a railroad rail surface of a railroad track, said tribometer comprising:

(a) a test cart being capable of riding the railroad track and testing the coefficient of friction of a railroad rail surface of the railroad track, said test cart including (i) a test cart frame having front and rear axle assemblies capable of supporting said test cart above the railroad track, and (ii) at least one rail test assembly having a rail testing wheel at one end, said at least one rail test assembly being capable of movement between a testing mode and a non-testing mode, said at least one rail test assembly in the testing mode placing said rail testing wheel in communication with the railroad rail surface, and said at least one rail test assembly in the non-testing mode removing said rail testing wheel from communication with the railroad rail surface;

(b) a motive system capable of moving said test cart along the railroad track; and (c) automated systems capable of both controlling said test cart, and measuring and recording various data relating to speed and location of said tribometer, and conditions of the railroad rail surface;

said test cart frame and said rail testing wheel providing a consistent and repeatable contact line on the railroad rail surface enabling a consistent and repeatable measurement of the coefficient of friction at the same location along the railroad rail surface.

34. The tribometer of claim 33, said test cart further comprising a braking system capable of braking said rail testing wheel during the testing mode of the at least one rail test assembly, said at least one rail test assembly having at least one tread test subassembly.

35. The tribometer of claim 33, said test cart further comprising a braking system capable of braking said rail testing wheel during the testing mode of the at least one rail test assembly, said at least one rail test assembly having at least one gauge test subassembly.

* * * * *